US008067371B2

(12) United States Patent
Schmidt et al.

(10) Patent No.: US 8,067,371 B2
(45) Date of Patent: Nov. 29, 2011

(54) RAGE G82S-RELATED METHODS AND COMPOSITIONS FOR TREATING INFLAMMATORY DISORDERS

(75) Inventors: Ann Marie Schmidt, Franklin Lakes, NJ (US); David M. Stern, Augusta, GA (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1503 days.

(21) Appl. No.: 10/840,927

(22) Filed: May 7, 2004

(65) Prior Publication Data
US 2005/0129682 A1   Jun. 16, 2005

Related U.S. Application Data (60) Provisional application No. 60/469,428, filed on May 9, 2003.

(51) Int. Cl.
*A61K 38/00* (2006.01)
(52) U.S. Cl. ..................... 514/12.2; 514/16.6
(58) Field of Classification Search .......... None
See application file for complete search history.

(56) References Cited

U.S. PATENT DOCUMENTS

| | | | |
|---|---|---|---|
| 5,741,486 A | 4/1998 | Pathak et al. | |
| 5,864,018 A * | 1/1999 | Morser et al. | 530/387.1 |
| 6,007,991 A | 12/1999 | Sivaraman et al. | |
| 6,071,890 A | 6/2000 | Scheule et al. | |
| 6,271,210 B1 | 8/2001 | Sivaraman et al. | |
| 6,465,422 B1 | 10/2002 | Schmidt et al. | |
| 6,503,887 B1 | 1/2003 | During | |
| 6,506,559 B1 | 1/2003 | Fire et al. | |
| 6,555,340 B1 | 4/2003 | Schmidt et al. | |
| 6,555,651 B2 | 4/2003 | Stern et al. | |
| 6,563,015 B1 | 5/2003 | Stern et al. | |
| 6,670,136 B2 | 12/2003 | Schmidt et al. | |
| 6,677,299 B2 | 1/2004 | Stern et al. | |
| 6,692,966 B2 | 2/2004 | Fallaux et al. | |
| 6,697,669 B2 | 2/2004 | Dev et al. | |
| 6,753,150 B2 | 6/2004 | Schmidt et al. | |
| 6,790,443 B2 | 9/2004 | Stern et al. | |
| 6,825,164 B1 | 11/2004 | Stern et al. | |
| 7,026,444 B2 | 4/2006 | Schmidt et al. | |
| 7,081,241 B1 | 7/2006 | Schmidt et al. | |
| 7,101,838 B2 | 9/2006 | Stern et al. | |
| 7,125,675 B2 | 10/2006 | Schmidt et al. | |
| 7,258,857 B2 * | 8/2007 | Stern et al. | 424/130.1 |
| 7,494,972 B2 | 2/2009 | Stern et al. | |
| 7,700,085 B2 | 4/2010 | Stern | |
| 7,732,400 B2 | 6/2010 | Stern et al. | |
| 2002/0122799 A1 | 9/2002 | Stern et al. | |
| 2004/0142391 A1 | 7/2004 | Schmidt | |
| 2005/0170382 A1 | 8/2005 | Stern | |
| 2006/0078562 A1 | 4/2006 | Mjalli | |
| 2007/0014791 A1 | 1/2007 | Schmidt | |
| 2007/0167360 A1 | 7/2007 | Yan et al. | |
| 2008/0019986 A1 | 1/2008 | Stern | |
| 2008/0207499 A1 | 8/2008 | Barile | |
| 2008/0214453 A1 | 9/2008 | Stern | |
| 2008/0260717 A1 | 10/2008 | Yan et al. | |
| 2009/0028882 A1 | 1/2009 | Stern | |
| 2009/0060925 A1 | 3/2009 | Mjalli | |
| 2009/0191210 A1 | 7/2009 | Schmidt | |
| 2009/0220484 A1 | 9/2009 | Schmidt | |
| 2009/0228997 A1 | 9/2009 | Stern et al. | |

FOREIGN PATENT DOCUMENTS

| | | |
|---|---|---|
| WO | WO 97/26913 | 7/1997 |
| WO | WO 99/54485 | 10/1997 |
| WO | WO 98/22138 | 5/1998 |
| WO | WO/99/07402 | 2/1999 |
| WO | WO 99/18987 | 4/1999 |
| WO | WO 00/20458 | 4/2000 |
| WO | WO/00/20621 | 4/2000 |
| WO | WO/01/12598 | 2/2001 |
| WO | WO/02/14519 | 2/2002 |
| WO | WO/02/30889 | 4/2002 |
| WO | WO/2004/100890 | 11/2004 |
| WO | WO/2005/023191 | 3/2005 |
| WO | WO/2005/042032 | 5/2005 |
| WO | WO/2005/427872 | 5/2005 |
| WO | WO/2006/017643 | 2/2006 |
| WO | WO/2006/099620 | 9/2006 |
| WO | WO/2008/153957 | 12/2008 |
| WO | WO/2009/058363 | 5/2009 |

OTHER PUBLICATIONS

Hofmann, M.A., Drury, S., Fu, C., et al. RAGE mediates a novel proinflammatory axis: a central cell surface receptor for S100/calgranulin polypeptides. *Cell* 1999; 97: 889-901.

Chilosi, M., Mombello, A., Montagna, L., et al. Multimarker immunohistochemical staining of calgranulin, chloroacetate esterase, and S100 for simultaneous demonstration of inflammatory cells on paraffin sections. *J. Histochem. Cytochem.* 1990; 38: 1669-1675.

Youssef, P., Roth, J., Frosch, M.P., et al. Expression of myeloid related proteins (MRP) 8 and 14 and the MRP8/14 heterodimer in rheumatoid arthritis synovial membrane. *J. Rheumatol.* 1990; 26: 2523-2528.

Frosch, M., Strey, A., Vogl, T., et al. Myeloid-related proteins 8 and 14 are specifically secreted during interaction of phagocytes and activated endothelium and are useful markers for monitoring disease activity in pauciarticular-onset juvenile rheumatoid arthritis. *Arthritis Rheum.* 2000; 43: 628-637.

Zimmer, D.B., Cornwall, E.H., Landar, A., Song, W., The S100 protein family: history, function, and expression. *Brain Research Bulletin* 1995; 37: 417-429.

Schafer, B.W., Heinzmann, C.W., The S100 family of EF-hand calcium-binding proteins: functions and pathology. *TIBS* 1996; 21: 134-140.

(Continued)

*Primary Examiner* — Daniel E Kolker
*Assistant Examiner* — Gregory S Emch
(74) *Attorney, Agent, or Firm* — John P. White; Cooper & Dunham LLP (57) ABSTRACT

This invention provides methods, compositions and articles of manufacture for inhibiting the onset of and treating inflammatory disorders such as rheumatoid arthritis. The instant invention is based on the blockade of RAGE G82S function.

15 Claims, 5 Drawing Sheets

OTHER PUBLICATIONS

Rammes, A., Roth, J., Goebeler, M., Klempt, M., Hartmann, M., Sorg, C., Myeloid-related protein (MRP) 8 and MRP14, calcium-binding proteins of the S100 family, are secreted by activated monocytes via a novel, tubulin-dependent pathway. *J. Biol. Chem.* 1997; 272: 9496-9502.

Hudson, B.I., Stickland, M.H., Grant, P.J., Identification of polymorphisms in the Receptor for Advanced Glycation End Products (RAGE) gene. *Diabetes* 1998; 47: 1155-1157.

Prevost, G., Fajardy, I., Fontaine, P., Danze, P.M., Besmond, C., Human RAGE Gly82Ser dimorphism and HLA class II DRB1-DQA1-DQB1 haplotypes in type 1 diabetes. *Europ. J. Immunogenet.* 1999; 26: 343-348.

Neeper, M., Schmidt, A.M., Brett, J., et al. Cloning and expression of RAGE: a cell surface receptor for advanced glycosylation end products of proteins. *J. Biol. Chem.* 1992; 267: 14998-15004.

Schmidt, A.M., Vianna, M., Gerlach, M., et al. Isolation and characterization of binding proteins for advanced glycosylation endproducts from lung tissue which are present on the endothelial cell surface. *J. Biol. Chem.* 1992; 267: 14987-14997.

Kislinger, T., Fu, C., Huber, B., et al. $N^\epsilon$ (carboxymethyl)lysine adducts of proteins are ligands for receptor for advanced glycation endproducts that activate cell signalling pathways and modulate gene expression. *J. Biol. Chem.* 1999; 274: 31740-31749.

Yan, S.D., Chen, X., Fu, J., et al. RAGE and amyloid beta peptide neurotoxicity in Alzheimer's disease. *Nature* 1996; 382: 685-691.

Hori, O., Brett, J., Slattery, T., et al. The receptor for advanced glycation endproducts (RAGE) is a cellular binding site for amphoterin: mediation of neurite outgrowth and coexpression of RAGE and amphoterin in the developing nervous system. *J. Biol. Chem.* 1995; 270: 25752-25761.

Courtenay, J.S., Dallman, M.J., Dayan, A.D., Martin, A., Mosedale, B., Immunization against heterologous type II collagen induces arthritis in mice. *Nature* 1980; 283: 666-668.

Trentham, D.E., Townes, A.S., Kang, A.H., Autoimmunity to type II collagen an experimental model of arthritis. *J. Exp. Med.* 1997; 146: 857-868.

Cathcart, E.S., Hayes, K.C., Gonnerman, W.A., Lazzari, A.A., Franzblau, C., Experimental arthritis in a nonhuman primate. I. Induction by bovine type II collagen. *Lab. Invest.* 1986; 54: 26-31.

Park, L., Raman, K.G., Lee, K.J., et al. Suppression of accelerated diabetic atherosclerosis by soluble Receptor for AGE (sRAGE). *Nature Medicine* 1998; 4: 1025-1031.

Quattrocchi, E., Walmsley, M., Browne, K., et al. Paradoxical effects of adenovirus-mediated blockade of TNF activity in murine collagen-induced arthritis. *J. Immunol.* 1999; 163: 1000-1009.

Neurath, M.F., Hildner, K., Becker, C., et al. Methotrexate specifically modulates cytokine production by T cells and macrophages in murine collagen-induced artjrotos (CIA): a mechanism for methotrexate-mediated immunosuppression. *Clin. Exp. Immunol.* 1999; 115: 42-55.

Pugin, J., Widmer, M.C., Kosodo, S., Liang, C.M., Preas, H.L. II, Suffredini, A.F., Human neutrophils secrete gelatinase B in vitro and in vivo in response to endotoxin and proinflammatory mediators. *Am. J. Respir. Cell Mol. Biol.* 1999; 20: 458-464.

Lander, H.L., Tauras, J.M., Ogiste, J.S., Moss, R.A., Schmidt, A.M., Activation of the Receptor for Advanced Glycation Endproducts triggers a MAP Kinase pathway regulated by oxidant stress. *J. Biol. Chem.* 1997; 272: 17810-17814.

Taguchi, A., Blood, D.C., del Toro, G.A., et al. Blockade of amphoterin/RAGE signalling suppresses tumor growth and metastases. *Nature 2000*; 405: 354-360.

Pisetsky, D.S., Tumor necrosis factor blockers in rheumatoid arthritis. *N. Engl. J. Med.* 2000; 342: 810-811.

Boe, A., Baiocchi, M., Carbonatto, M., Papoian, R., Serlupi-Crescenzi, O., Interleukin-6 knock-out mice are resistant to antigen-induced experimental arthritis. *Cytokine* 1999; 11: 1057-1064.

Robak, T., Gladalska, A., Stepien, H., Robak, E., Serum levels of interleukin-6 type cytokines and soluble interleukin-6 receptor in patients with rheumatoid arthritis. *Mediators Inflamm* 1998; 7: 347-353.

Keyszer, G., Lambiri, I., Nagel, R., et al. Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers. *J. Rheumatol.* 1999; 26: 251-258.

Konttinen, Y.T., Ainola, M., Valleala, H., et al. Analysis of 16 different matrix metalloproteinases (MMP-1 to MMP-20) in the synovial membrane: different profiles in trauma and rheumatoid arthritis. *Ann. Rheum. Dis.* 1999; 58: 691-697.

Iwaki-Egawa, S., Watanabe, Y., Matsuno, H. Correlations between matrix metalloproteinase-9 and adenosine deaminase isozymes in synovial fluid from patients with rheumatoid arthritis. J. Rheumatol. 2001; 28: 485-489.

Kaneko, O., Tomita, T., Nakase, T., et al. Expression of proteinases and inflammatory cytokines in subchondral bone regions in the destructive joint of rheumatoid arthritis. *Rheumatology* 2001; 40: 247-255.

Meyer, J.M., Han, J., Singh, R., Moxley, G., Sex influences on the penetrance of HLA shared-epitope genotypes for rheumatoid arthritis. *Am. J. Hum. Genet.* 1996; 58: 371-383.

Gregersen, P.K., Silver, J., Winchester, R.J., The shared epitope hypothesis. An approach to understanding the molecular genetics of susceptibility to rheumatoid arthritis. *Arthritis Rheum.* 1987; 30: 1205-1213.

Stastny, P., Association of the B-cell autoantigen DRW4 with rheumatoid arthritis. *N. Engl. J. Med.* 1978; 298: 869-871.

Sugaya, K., Fukagawa, T., Matsumoto, K., et al. Three genes in the MHC Class III region near the junction with the class II: gene for Receptor of Advanced Glycosylation End Products, PBX2 homeobox gene and a notch homolog, human counterpart of mouse mammary tumor gene *int-3*. *Genomics* 1994; 23: 408-419.

Donato, R., S100: a multigenic family of calcium-modulated proteins of the EF-hand type with intracellular and extracellular functional roles. *Intl. J. Biochem. Cell. Biol.* 2001; 33: 637-668.

Lugering, N., Stoll, R., Schmid, K.W., et al. The myeloic related protein MRP8/14 (27E10 antigen)-usefulness as a potential marker for disease activity in ulcerative colitis and putative biological function. *Europ. J. Clin. Invest.* 1995; 25: 659-664.

Schmid, K.W., Lugering, N., Stoll, R., et al. Immunohistochemical demonstration of calcium-binding proteins MRP8 and MRP 14 and their heterodimer (27E10 antigen) in Crohn's disease. *Human Pathol.* 1995; 26: 334-337.

Madsen, P., Molecular cloning, occurrence and expression of a novel partially secreted protein "psoriasin" that is highly up-regulated in psoriatic skin. *J Invest Dermatol* 1991; 97: 701-712.

Gregersen, P.K., The North American Rheumatoid Arthritis Consortium—bringing genetic analysis to bear on disease susceptibility, severity and outcome. *Arthritis Care* 1998; 11: 1-2.

Cornelis, F., Faure, S., Martinez, M., et al. New susceptibility locus for rheumatoid arthritis suggested by a genome-wide linkage study. *Proc. Natl. Acad. Sci. USA* 1998; 95: 10746-10750.

Weyand, C.M., Hicok, K.C., Conn, D.L., Goronzy, J.J. The influence of HLA-DRB1 genes on disease severity in rheumatoid arthritis. *Ann. Int. Med.* 1992; 117: 801-806.

Eberhardt, K., Fex, E., Johnson, U., Wollheim, F.A., Associations of HLA-DRB and -DQB genes with two and five year outcomes in rheumatoid arthritis. *Ann. Rheum. Dis.* 1996; 55: 34-39.

Reveille, J.D., Alarcon, G.S., Fowler, S.E., et al. HLA-DRB1 genes and disease severity in rheumatoid arthritis. *Arthritis Rheum.* 1996; 39: 1802-1807.

Criswell, L.A., Mu, H., Such, C.L., King, M.C., Inheritance of the shared epitope and long-term outcomes of rheumatoid arthritis among community-based Caucasian females. *Genet. Epidemiol.* 1998; 15: 61-72.

Weyand, C.M., McCarthy, T.G., Goronzy, J.J., Correlation between disease phenotype and genetic heterogeneity in rheumatoid arthritis. *J. Clin. Invest.* 1995; 95: 2120-2126.

Hall, F.C., Weeks, D.E., Camillieri, J.P., et al. Influence of the HLA-DRB1 locus on susceptibility and severity in rheumatoid arthritis. *Q.J.M.* 1996; 89: 821-829.

Mattey, D.L., Hassell, A.B., Plant, M.J., et al. The influence of HLA-DRB1 alleles encoding the DERAA amino acid motif on radiological outcome in rheumatoid arthritis. *Rheumatology* (Oxford) 1999; 38: 1221-1227.

Seitz, M., Perler, M., Pichler, W., Only weak association between disease severity and HLA-DRB1 genes in a Swiss population of rheumatoid arthritis patients. *Rheumatol. Int.* 1996; 16: 9-13.

Suarez-Almazor, M.E., Tao, S., Moustarah, F., Russell, A.S., Maksymowych, W., HLA-DR1, DR4, and DRB1 disease related subtypes in rheumatoid arthritis. Association with susceptibility but not severity in a city-wide community based study. *J. Rheumatol.* 1995; 22: 2027-2033.

Harrison, B., Thomson, W., Symmons, D., et al. The influence of HLA-DRB1 alleles and rheumatoid arthritis on disease outcome in an inception cohort of patients with early inflammatory arthritis. *Arthritis Rheum.* 1999; 42: 2174-2183.

Mulcahy, B., Waldron-Lynch, F., McDermott, M.F., et al. Genetic variability in the tumor necrosis factor-lymphtoxin region influences susceptibility to rheumatoid arthritis. *Am. J. Hum. Genet.* 1996; 59: 676-683.

Ota, M., Katsuyama, Y., Kimura, A., et al. A second susceptibility gene for developing rheumatoid arthritis in the human MHC is localized within a 70-kb interval telomeric of the TNF genes in the HLA class III region. *Genomics* 2001; 71: 263-270.

Complete sequencing and gene map of a human major histocompatibility complex. The MHC sequencing consortium. *Nature* 1999; 401: 921-923.

Hudson, B.I., Stickland, M.H., Futers, T.S., Grant, P.J., Effects of novel polymorphisms in the RAGE gene on transcriptional regulation and their association with diabetic retinopathy. *Diabetes* 2001; 50: 1505-1511.

Lalla, E., Lamster, I.B., Feit, M., et al. Blockade of RAGE suppresses periodontitis-associated alveolar bone loss in diabetic mice. *J. Clin. Invest.* 2000; 105: 1117-1124.

Kankova, K., Zahejsky, J., Marova, I., et al. Polymorphisms in the RAGE gene influence susceptibility to diabetes-associated microvascular dermatoses in NIDDM. *J. Diabetes Complications* 2001; 15: 185-192.

Klotz, I., Hunston, D., Mathematical models for ligand-receptor binding. *J. Biol. Chem.* 1984; 259: 10060-10062.

Arnett, F.C., Edworthy, S.M., Bloch, D.A., et al. The American Rheumatism Association 1987 revised criteria for the classification of rheumatoid arthritis. *Arthritis Rheum.* 1988; 31: 315-324.

Svejgaard, A., Ryder, L.P., HLA and disease associations: detecting the strongest association. *Tissue Antigens* 1994; 43: 18-27.

Tiwari, J.L., Terasaki, P.I., The data and statistical analysis. In: Tiwari JL, Terasaki PI (eds). *HLA and Disease Associations*. Springer-Verlag, New York, 1985, pp. 18-22.

International Search Report issued in connection with related PCT Patent Application No. PCT/US04/14476, on behalf of The Trustees of Columbia University in the City of New York filed May 7, 2004.

Hofmann, et al., "RAGE and arthritis: The G82S polymorphism amplifies the inflammatory response," Genes Immunity vol. 3, pp. 123-135 (2002).

U.S. Appl. No. 08/997,464, filed Dec. 23, 1997 for Stern et al.
U.S. Appl. No. 09/687,528, filed Oct. 13, 2000 for Stern et al.
U.S. Appl. No. 09/638,653, filed Aug. 14, 2000 for Stern et al.
U.S. Appl. No. 08/592,070, filed Jan. 26, 1996, for Stern et al.
U.S. Appl. No. 11/584,310, filed Oct. 20, 2006, for Schmidt et al.
U.S. Appl. No. 11/801,635, filed May 9, 2007, for Stern et al.
U.S. Appl. No. 12/799,204, filed Apr. 20, 2010, for Stern et al.
U.S. Appl. No. 09/498,459, filed Feb. 4, 2000, for Stern et al.
U.S. Appl. No. 12/802,485, filed Jun. 7, 2010, for Stern et al.
Pending claims for U.S. Appl. No. 08/592,070, filed Jan. 26, 1996, for Stern et al.
Pending claims for U.S. Appl. No. 11/584,310, filed Oct. 20, 2006, for Schmidt et al.
Pending claims for U.S. Appl. No. 11/801,635, filed May 9, 2007, for Stern et al.
Pending claims for U.S. Publication No. 2009/0228997 A1, published Sep. 10, 2009, for Stern.
Pending claims for U.S. Patent Publication No. 2009/0191210 A1, published Jul. 30, 2009, for Schmidt.
Pending claims for U.S. Patent Publication No. 2008/0019986, published Jan. 24, 2008, for Stern.
Pending claims for U.S. Patent Publication No. 2009/0028882 A1, published Jan. 29, 2009, for Stern.
Pending claims for U.S. Patent Publication No. 2008/0214453, published Sep. 4, 2008, for Stern.
Pending claims for U.S. Patent Publication No. 2008/0260717 A1, published Oct. 23, 2008, for Yan et al.
Pending claims for U.S. Patent Publication No. 2009/0220484 A1, published Sep. 3, 2009, for Schmidt.
Pending claims for U.S. Patent Publication No. 2008/0207499, published Aug. 28, 2008, for Barile.
Pending claims for U.S. Patent Publication No. 2006/0078562, published Apr. 13, 2006, for Mjalli.
Pending claims for U.S. Patent Publication No. 2009/0060925 A1, published Mar. 5, 2009, for Mjalli.
Pending claims for U.S. Appl. No. 12/799,204, filed Apr. 20, 2010, for Stern et al.
Pending claims for U.S. Appl. No. 09/498,459, filed Feb. 4, 2000, for Stern et al.
Pending claims for U.S. Appl. No. 12/802,485, filed Jun. 7, 2010 for Stern et al.

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: sense primer used to detect G82S polymorphism
      of RAGE gene

<400> SEQUENCE: 1
gtaagcgggg ctcctgttgc a                                              21

<210> SEQ ID NO 2
<211> LENGTH: 21
<212> TYPE: DNA
<213> ORGANISM: Artificial Sequence
<220> FEATURE:
<223> OTHER INFORMATION: antisense primer used to detect G82S
      polymorphism of RAGE gene

<400> SEQUENCE: 2
ggccaaggct ggggttgaag g                                              21
```

RAGE G82S-RELATED METHODS AND COMPOSITIONS FOR TREATING INFLAMMATORY DISORDERS

This application claims the benefit of U.S. Provisional Application No. 60/469,428, filed May 9, 2003, the contents of which are hereby incorporated by reference.

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

BACKGROUND OF THE INVENTION

The Receptor for Advanced Glycation Endproducts ("RAGE"), a multi-ligand member of the immunoglobulin superfamily of cell surface molecules, has been implicated in amplification of proinflammatory responses (1). S100/calgranulins, proinflammatory signal transduction ligands of the receptor, are enriched in joints of subjects with rheumatoid arthritis ("RA") (2-4). Members of this family of molecules, long-associated with classic immune/inflammatory disorders (5-6), may be released by activated inflammatory effector cells such as monocytes (7), thereby freeing them to engage cell surface RAGE and amplify host inflammatory responses. Indeed, accumulation of S100/calgranulins in synovial fluid and plasma of subjects with RA has been correlated with indices of disease severity, such as bony erosions (4).

Recent studies have highlighted the possibility that polymorphisms within key domains of RAGE may influence its function, so that under conditions of increased ligand accumulation, individuals may be predisposed to heightened inflammatory responses (8-9). Importantly, a polymorphism of the RAGE gene has been identified within the V-type immunoglobulin domain in the extracellular region of the receptor, consisting of a glycine to serine change at position 82 (8). In previous studies, it was found that the ligands of RAGE, including S100/calgranulins, engage the V-domain of the receptor and activate signal transduction pathways, thereby modulating gene expression (1,10-14).

SUMMARY OF THE INVENTION

This invention provides a method for inhibiting binding between RAGE and a ligand thereof comprising contacting the RAGE with an agent comprising soluble RAGE G82S, a ligand-binding portion of soluble RAGE G82S, or an antibody directed to RAGE G82S.

This invention further provides a method for inhibiting binding between RAGE G82S and a ligand thereof comprising contacting the RAGE G82S with an agent comprising soluble RAGE G82S, a ligand-binding portion of soluble RAGE G82S, or an antibody directed to RAGE G82S.

This invention further provides a method for treating an inflammatory disorder in a subject comprising administering to the subject a therapeutically effective amount of an agent that inhibits binding between RAGE G82S and a ligand thereof.

This invention further provides a method for inhibiting the onset of an inflammatory disorder in a subject comprising administering to the subject a prophylactically effective amount of an agent that inhibits binding between RAGE G82S and a ligand thereof.

This invention further provides soluble RAGE G82S or a ligand-binding portion thereof. This invention further provides a composition comprising a pharmaceutically acceptable carrier and (i) soluble RAGE G82S, (ii) a ligand-binding portion of soluble RAGE G82S, and/or (iii) a nucleic acid which specifically inhibits the expression of RAGE G82S in a cell expressing-same.

This invention further provides a method for inhibiting the onset of an inflammatory disorder in a subject comprising administering to the subject a prophylactically effective amount of a nucleic acid which specifically inhibits the expression of RAGE G82S in the subject's cells expressing same.

This invention further provides a method for treating a subject afflicted with an inflammatory disorder comprising administering to the subject a therapeutically effective amount of a nucleic acid which specifically inhibits the expression of RAGE G82S in the subject's cells expressing same.

Finally, this invention provides an article of manufacture comprising a packaging material having therein (i) an agent that inhibits binding between RAGE G82S and a ligand thereof and/or (ii) a nucleic acid which specifically inhibits the expression of RAGE G82S in a cell expressing same, wherein the packaging material has affixed thereto a label indicating a use for the agent and/or nucleic acid for treating an inflammatory disorder in a subject.

BRIEF DESCRIPTION OF THE FIGURES

FIGS. 1A-1N. Induction of arthritis by bovine type II collagen in DBA/1 mice: increased expression of RAGE and S100/calgranulins. Six weeks after immunization (day 42), joint tissue from the hind feet (a-l) or stifle joint (m-n) was prepared for study.

1A-1L. Histology. In a-b-c, tissue was subjected to H&E analysis. Immunohistochemistry using anti-RAGE IgG (d-e-f); anti-S100/calgranulin IgG (g-h-i); or rabbit nonimmune IgG (j-k-l) was performed. Scale bar: a-b-c, 300 µm; and d-l, 60 µm.

1M-1N. Immunoblotting. Lysates were prepared from stifle joints and subjected to immunoblotting using anti-RAGE IgG (m); or anti-S100/calgranulin IgG (n) N=5 mice per condition were employed. Densitometric analysis of band intensity from all mice in each group was performed, and the mean±SD is shown. Representative bands are shown. Statistical considerations are indicated in the figure.

FIGS. 2A-2D. Blockade of RAGE suppresses inflammation in DBA/1 mice immunized/challenged with bovine type II collagen.

2A. Clinical score. At the indicated times after immunization with bovine type II collagen and treatment with murine sRAGE or vehicle (murine serum albumin (MSA) or PBS), clinical scoring was performed by blinded observers. The mean±standard deviation (SD) is shown; n=10 mice per group. * indicates p<0.05.

2B. Histologic score. Histologic scoring of joints in four limbs was performed on H&E-stained sections from mice six weeks after immunization. The mean±SD is shown; n=10 mice per group. * indicates p<0.05.

2C. Ear swelling. Six weeks after immunization with bovine type II collagen, murine serum albumin (MSA)-, PBS- and sRAGE-treated mice were injected with bovine type II collagen into ear tissue. Ear thickness was measured by a blinded observer immediately prior to local injection, and 18 hrs later. The mean±SD is shown; n=5 mice per group. * indicates p<0.05 vs ear thickness in PBS- and MSA-treated groups.

2D. Antibody response to bovine, type II collagen. At the, indicated time points after immunization, plasma was retrieved from DBA/1 mice and subjected to ELISA for determination of total serum IgG levels to type II collagen. There were no statistically-significant differences in total IgG levels among the groups.

FIGS. 3A-3F. Blockade of RAGE suppresses generation of cytokines and MMPs in DBA/1 mice immunized/challenged with bovine type II collagen.

3A-3B. Joint tissue. Stifle joint tissue was retrieved six weeks after immunization with bovine type II collagen. Lysates were subjected to ELISA for detection of murine. TNF-alpha (a) and IL-6 (b). Results were normalized per mg/tissue extract.

3C-3D. Plasma. Plasma from mice was subjected to ELISA for levels of TNF-alpha (c) and IL-6 (d). In a-b-c-d, n=10 mice per group. The mean±SD is shown. In a-d, * indicates p<0.05.

3E-3F. Zymography. Stifle joint tissue was retrieved and lysates were prepared and zymography for detection of activity of MMP-2, -9 or -13 was performed. N=10 mice/group. Densitometric analysis of band intensity from all mice/groups was performed, and the mean±SD is shown. Representative bands are shown. In f, * indicates p<0.05 vs MSA-treated mice with collagen-induced arthritis.

FIGS. 4A-4F. CHO cells bearing RAGE 82S display increased affinity and cellular responsiveness to EN-RAGE. CHO cells, which endogenously do not express RAGE antigen, were stably-transfected with pcDNA3.1 vector containing cDNA encoding human RAGE 82G or the variant allele 82S.

4A. Immunoblotting. Lysates of stably-transfected CHO cells were prepared and subjected to immunoblotting using anti-human RAGE IgG.

4B-4C. Radioligand binding assays. Purified EN-RAGE was radiolabelled using $^{125}$-I and radioligand binding assays were performed in 96-well tissue culture dishes containing the indicated transfected CHO cells. Equilibrium binding data were analyzed according to the equation of Klotz and Hunston. Where indicated, pretreatment with either antibodies, human soluble RAGE or bovine serum albumin was performed. The mean±standard deviation (SD) is shown. In c, * indicates p<0.01 versus respective controls.

4D-4E. Activation of MEK 1/2 and p44/p42 MAP kinases. The indicated stably-transfected CHO cells were incubated with EN-RAGE for one hr. Immunoblotting of cell lysates was performed using anti-phosphorylated MEK 1/2 (d) or p44/p42 MAP kinase (e). Where indicated, pretreatment with either BSA or sRAGE, or the indicated IgG for 2 hrs was performed. Control immunoblotting using antibody to total MEK 1/2 and p44/p42 MAP kinase revealed that there were no differences in levels of total MEK 1/2 or p44/p42 (not shown).

4F. Activation of NF-kB. Nuclear extracts were prepared from the indicated stably-transfected CHO cells incubated with EN-RAGE for 6 hrs and EMSA was performed. Where indicated, cells were pretreated with either nonimmune/anti-RAGE IgG, soluble RAGE or BSA for 2 hrs prior to incubation with EN-RAGE. In d-e-f, bands were scanned into a densitometer, and band density was quantified using. ImageQuant. These experiments were performed at least three times and subjected to statistical analyses as indicated in the text and the figure legend. Representative experiments are shown.

FIGS. 5A-5H. Human peripheral blood mononuclear phagocytes (MPs) expressing RAGE 82S display increased responsiveness to EN-RAGE. MPs were purified from the blood of human subjects bearing RAGE (G82G) (n=5) or heterozygotes (G82S) (n=5).

5A-5D. Activation of MEK 1/2 and p44/p42 MAP kinases. The indicated MPs were incubated with EN-RAGE or no mediator for one hr. Cell lysates were prepared and immunoblotting performed using anti-phosphorylated MEK 1/2 (a,b) or p44/p42 MAP kinase (c,d) Densitometric analysis was performed and mean±SD is shown in b and d. Immunoblotting using antibody to total MEK 1/2 and p44/p42 MAP kinase revealed that there were no differences in levels of total MEK 1/2 or p44/p42 (not shown).

5E-5F. Generation of TNF-alpha and IL-6. Human MPs bearing the indicated RAGE alleles were cultured in the presence of either no mediator or EN-RAGE for 14 hrs. Supernatants were retrieved and levels of TNF-alpha (e) and IL-6 (f) determined by ELISA. The mean±SD is shown.

5G-5H. MMP-9 activity. Human MPs bearing the indicated. RAGE alleles were cultured in the presence of either no mediator or. EN-RAGE for 14 hrs. Supernatants were retrieved and subjected to zymography to assess levels of activated MMP-9. In b, d, and h, bands from n=5 G82G and n=5 G82S subjects were scanned into a densitometer and band density was quantified. Representative experiments are shown. The mean±SD is shown. In b,d,e,f and h, * indicates p<0.01 versus baseline.

DETAILED DESCRIPTION OF THE INVENTION

Definitions

"Antibody" shall include, by way of example, both naturally occurring and non-naturally occurring antibodies. Specifically, this term includes polyclonal and monoclonal antibodies, and antigen-binding fragments thereof. Furthermore, this term includes chimeric antibodies and wholly synthetic antibodies, and antigen-binding fragments thereof.

"Anti-sense nucleic acid" shall mean any nucleic acid which, when introduced into a cell, specifically hybridizes to at least a portion of an mRNA in the cell encoding a protein ("target protein") whose expression is to be inhibited, and thereby inhibits the target protein's expression.

"Catalytic nucleic acid" shall mean a nucleic acid that specifically recognizes a distinct substrate and catalyzes the chemical modification of this substrate. Catalytic nucleic acids include, for example, DNAzymes and ribozymes.

"DNAzyme" shall mean a catalytic nucleic acid that is DNA or whose catalytic component is DNA, and which specifically recognizes and cleaves a distinct target nucleic acid sequence, which can be either DNA or RNA. Each DNAzyme has a catalytic component (also referred to as a "catalytic domain") and a target sequence-binding component consisting of two binding domains, one on either side of the catalytic domain.

"Expressible nucleic acid" shall mean a nucleic acid encoding a nucleic acid of interest and/or a protein of interest, which nucleic acid is an expression vector, plasmid or other construct which, when placed in a cell, permits the expression of the nucleic acid or protein of interest. Expression vectors and plasmids are well known in the art.

As used herein, "inflammatory disorder" includes, without limitation, any disorder possessing an inflammatory component. Examples of inflammatory disorders include autoimmune disorders generally, rheumatoid arthritis, amyotrophic lateral sclerosis, vascular disorders (e.g. atherosclerosis or transplant vasculopathy), and diabetes.

As used herein, "inhibit," when used in connection with the binding between RAGE and/or RAGE G82S with a ligand thereof, shall mean to reduce such binding. In one embodiment, "inhibit" shall mean to eliminate such binding.

"Inhibiting" the onset of a disorder shall mean either lessening the likelihood of the disorder's onset, or preventing the onset of the disorder entirely. In the preferred embodiment, inhibiting the onset of a disorder means preventing its onset entirely.

"Nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

"Ribozyme" shall mean a catalytic nucleic acid molecule which is. RNA or whose catalytic component is. RNA, and which specifically recognizes and cleaves a distinct target nucleic acid sequence, which can be either DNA or RNA. Each ribozyme has a catalytic component (also referred to as a "catalytic domain") and a target sequence-binding component consisting of two binding domains, one on either side of the catalytic domain.

"Specifically hybridize" to a nucleic acid shall mean, with respect to a first nucleic acid, that the first nucleic acid hybridizes to a second nucleic acid with greater affinity than to any other nucleic acid.

"Specifically inhibit" the expression of a protein shall mean to inhibit that protein's expression (a) more than the expression of any other protein, or (b) more than the expression of all but 10 or fewer other proteins.

"Subject" shall mean any animal, such as a human, non-human primate, mouse, rat, guinea pig or rabbit.

"Treating" a disorder shall mean slowing, stopping or reversing the disorder's progression. In the preferred embodiment, treating a disorder means reversing the disorder's progression, ideally to the point of eliminating the disorder itself. As used herein, ameliorating a disorder and treating a disorder are equivalent.

Embodiments of the Invention

This invention provides methods for inhibiting binding between RAGE G82S with a ligand thereof, and for inhibiting the onset of and treating inflammatory disorders such as rheumatoid arthritis. This invention is based on the surprising discovery of a correlation between suppressing rheumatoid arthritis and blocking RAGE and/or RAGE G82S function.

Specifically, this invention provides a method for inhibiting binding between RAGE and a ligand thereof comprising contacting the RAGE with an agent comprising (i) soluble RAGE G82S, (ii) a ligand-binding portion of soluble RAGE G82S, or (iii) an antibody directed to RAGE G82S. This invention also provides a method for inhibiting binding between RAGE G82S and a ligand thereof comprising contacting the RAGE G82S with an agent comprising (i) soluble RAGE G82S, (ii) a ligand-binding portion of soluble RAGE G82S, or (iii) an antibody directed to RAGE G82S.

In one embodiment of the instant methods, the agent comprises soluble RAGE G82S. In another embodiment, the agent comprises a ligand-binding portion of soluble RAGE G82S. The ligand-binding portion can include, for example, amino acid residues 1-112 of RAGE G82S, and the V-domain. In a further embodiment, the agent comprises an antibody to RAGE G82S. In yet a further embodiment, the agent comprises a small molecule such as an organic molecule.

This invention also provides a method for treating an inflammatory disorder in a subject comprising administering to the subject a therapeutically effective amount of an agent that inhibits binding between RAGE G82S and a ligand thereof. This invention also provides a method for inhibiting the onset of an inflammatory disorder in a subject comprising administering to the subject a prophylactically effective amount of an agent that inhibits binding between RAGE G82S and a ligand thereof.

In the preferred embodiment of the instant methods, the subject is human. In one embodiment the inflammatory disorder is rheumatoid arthritis. In one embodiment of the instant methods, the agent comprises soluble RAGE G82S. In another embodiment, the agent comprises a ligand-binding portion of soluble RAGE G82S. In a further embodiment, the agent comprises an antibody to RAGE G82S. In yet a further embodiment, the agent comprises a small molecule such as an organic molecule.

Determining a therapeutically or prophylactically effective amount of agent can be done based on animal data using routine computational methods. In one embodiment, the therapeutically or prophylactically effective amount contains between about 1 ng and about 1 g of nucleic acid or protein, as applicable. In another embodiment, the effective amount contains between about 10 ng and about 100 mg of nucleic acid or protein, as applicable. In a further embodiment, the effective amount contains between about 100ng and about 10 mg of the nucleic acid or protein, as applicable. In a yet a further embodiment, the effective amount contains between about 1 µg and about 1 mg of the nucleic acid or protein, as applicable. In a yet a further embodiment, the effective amount contains between about 10µg and about 100µg of the nucleic acid or protein, as applicable. In a yet a further embodiment, the effective amount contains between about 100µg and about 10 mg of the nucleic acid or protein, as applicable.

In this invention, administering agents can be effected or performed using any of the various methods and delivery systems known to those skilled in the art. The administering can be performed, for example, intravenously, orally, via implant, transmucosally, transdermally, intramuscularly, and subcutaneously. The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

In one embodiment of this invention, the delivery system used comprises more than water alone, or more than buffer alone.

This invention further provides a method for inhibiting the onset of an inflammatory disorder in a subject comprising administering to the subject a prophylactically effective amount of a nucleic acid which specifically inhibits the expression of RAGE G82S in the subject's cells expressing same. This invention further provides a method for treating a subject afflicted with an inflammatory disorder comprising administering to the subject a therapeutically effective amount of a nucleic acid which specifically inhibits the expression of RAGE G82S in the subject's cells expressing same.

In the preferred embodiment the subject is human. In a one embodiment the inflammatory disorder is rheumatoid arthritis., In one embodiment the nucleic acid is DNA. In another embodiment the nucleic acid is RNA. In a further embodiment the nucleic acid is an anti-sense nucleic acid that specifically hybridizes to mRNA encoding RAGE G82S. In yet a further embodiment the nucleic acid is a catalytic nucleic acid that cleaves mRNA encoding RAGE G82S. In yet a further embodiment the nucleic acid is an expressible nucleic acid encoding an anti-sense nucleic acid that specifically hybridizes to mRNA encoding RAGE G82S. In yet a further embodiment the nucleic acid is an expressible nucleic acid encoding a catalytic nucleic acid that cleaves mRNA encoding RAGE G82S. In one embodiment the subject's cells in which the amount of RAGE G82S is to be reduced are cells which mediate an inflammatory reaction.

This invention further provides soluble RAGE G82S, a ligand-binding portion thereof, nucleic acids encoding same, and anti-RAGE G82S antibodies. The sequence of human RAGE is known (10, 11, and 61), as are ligand-binding portions thereof (62, 63).

This invention further provides a composition comprising a pharmaceutically acceptable carrier and (i) soluble RAGE G82S, (ii) a ligand-binding portion of soluble RAGE G82S, and/or (iii) a nucleic acid which specifically inhibits the expression of RAGE G82S in a cell expressing same. Making and using nucleic acids to selectively inhibit protein expression is known, as exemplified, for example, in patents relating to gene therapy (64-68), anti-sense therapy (69 and 70) and dsRNA use (71).

Finally, this invention provides an article of manufacture comprising a packaging material having therein (i) an agent that inhibits binding between RAGE G82S and a ligand thereof and/or (ii) a nucleic acid which specifically inhibits the expression of RAGE G82S in a cell expressing same, wherein the packaging material has affixed thereto a label indicating a use for the agent and/or nucleic acid for treating an inflammatory disorder in a subject.

In the preferred embodiment of the instant article of manufacture, the subject is human. In one embodiment of the invention, the disorder is rheumatoid arthritis and the agent comprises soluble RAGE G82S, a ligand-binding portion of soluble RAGE G82S, or an antibody directed to RAGE G82S. In one embodiment of the instant article of manufacture, the agent comprises soluble RAGE G82S. In another embodiment, the agent comprises a ligand-binding portion of soluble RAGE G82S. In a further embodiment, the agent comprises an antibody to RAGE G82S. In yet a further embodiment, the agent comprises a small molecule such as an organic molecule.

This invention is illustrated in the Experimental Details section which follows. This section is set forth to aid in an understanding of the invention but is not intended to, and should not be construed to, limit in any way the invention set forth in the claims which follow.

EXPERIMENTAL DETAILS

Murine Model of Bovine Collagen Type II-induced Arthritis

Induction of arthritis. Male DBA/1 mice were purchased from the Jackson Laboratories (Bar Harbor, Me.). On day 0, mice weighing 20-30 gms were injected intradermally at the base of the tail with bovine type II collagen, 200 μg (Sigma), dissolved in acetic acid (0.01M) and emulsified in complete Freund's adjuvant (ICN Biochemcials, Costa Mesa, Calif.). Three weeks later (day 22), mice were challenged by injection of bovine collagen type II (200 μg) in incomplete Freund's adjuvant (15-17). Beginning three weeks after immunization (day 22), mice were treated with murine soluble RAGE (1) (100 μg per day by intraperitoneal route). Vehicle treatment consisted of murine serum albumin (Sigma), 100 μg per day by intraperitoneal injection, or equal volumes of phosphate-buffered saline (PBS). Treatment was continued daily until sacrifice. All murine studies were performed in accordance with the policies of Columbia University's Institutional Animal Care and Use Committee.

Determination of anti-collagen IgG. ELISA was performed to determine levels of IgG to bovine type II collagen in dba/1 mice. Plastic Maxi-sorp 96-well plates (Nunc, Naperville, Ill.) were coated with bovine type II collagen (5 μg/ml) in bicarbonate/carbonate buffer; pH 9.3 for 16 hrs at 4° C. Unbound sites were blocked with PBS containing BSA (1%) for 8 hours at 4° C. Wells were washed five times in PBS and then incubated for 16 hrs in samples of mouse plasma (dilution, 1:50) in PBS at 4° C. Wells were washed five times with PBS and incubated with PBS containing 1% BSA and horse radish peroxidase-labelled anti-mouse IgG (Sigma; 1:500 dilution) for two hours at room temperature. Wells were washed with PBS five times and developed using o-phenylenediamine dihydrochloride (Sigma). A standard curve was prepared using serial dilutions from a mouse antibody cocktail against bovine type II collagen (Chemicon, Temecula, Calif.).

Assessment of arthritis. Arthritis was evaluated by clinical and histologic scoring by observers blinded to the experimental conditions. Clinical severity of arthritis in each of four limbs was assessed by the following scale (19): 0=normal; 1=slight erythema and swelling; 2=pronounced edematous swelling; and 3=joint deformity with ankylosis, resulting in a maximum score of 12 per animal. Histologic scoring of arthritis and cartilage and bone destruction was performed on hematoxylin and eosin-stained sections of extremity joints by the following scale (20): (i) synovial lesions: 0, no lesions; 1: mild effect; 2: moderate effect/proliferation; 3: severe lesions with destruction; (ii) cartilage destruction: 0, none; 1, mild; 2, moderate; 3, severe destruction with loss or complete fragmentation of cartilage; and (iii) bone destruction: 0, none; 1, mild destruction of subchondral bone; 2, moderate destruction; and 3, severe destruction with loss of large areas of bone. In other studies, six weeks after initial sensitization, bovine type II collagen (10 µg) was injected into the ear of each mouse. 18 hrs later, thickness of the ear was assessed using calipers by an observer blinded to the experimental conditions.

Immunoblotting and ELISA. Mice were sacrificed 3 or 6 weeks after challenge. The stifle joint was removed and homogenized in tris-buffered saline containing protease inhibitors (Complete Protease Inhibitor, Boehringer-Mannheim, Indianapolis, Ind.). SDS-PAGE and immunoblotting were performed on extracts of stifle joint tissue using the following antibodies: anti-RAGE IgG and anti-S100/calgranulin IgG as previously described (1) (4.7 and 2.0 µg/ml, respectively). ELISA for TNF-alpha and IL-6 was performed using kits from R&D Systems (Minneapolis, Minn.).

Zymography. Zymography for detection of MMP-3,9' and 13 activity was performed using gelatin or casein-laden gels from Novex/Invitrogen (Carlsbad, Calif.).

Chinese Hamster Ovary (CHO) Cell Studies

Chinese hamster ovary (CHO) cells were obtained from ATCC (Rockville, Md.) and cultured in F12 medium containing fetal bovine serum (10%)<(Life Technologies). To generate the 82S allele, the cDNA encoding human RAGE (10) was cloned using the TOPO TA cloning system into pCR2.1TOPO vector for mutagenesis (Invitrogen, Carlsbad, Calif.). Site-directed mutagenesis to insert the (-82G-) to (-82S-) change was performed using the GeneEditor In Vitro SDM System (Promega, Madison, Wis.). Sequencing was performed using an ABI310 automated DNA sequencer (Perkin Elmer Biosystems, Foster City, Calif.) to confirm the inserted sequence changes and to ensure that no other mutations were created. RAGE 82G and 82S cDNAs were excised from pCR2.1TOPO using EcoR I and subcloned into the pcDNA3.1 expression vector (Invitrogen). Cells were transfected with plasmid DNA using lipofectamine (Life Technologies) encoding the following: pcDNA3.1 containing full-length RAGE cDNA (-82G-), pcDNA3.1 containing. RAGE cDNA (-82S-), or pcDNA3.1 containing no insert (mock). 24 hrs after transfection, selection was begun using G418 (1 mg/ml) (Life Technologies). RAGE expression was assessed by immunoblotting in stably-transfected cells after 6 weeks. Cells were incubated with EN-RAGE (Extracellular Newly-Identified RAGE binding protein), a prototypic S100/calgranulin molecule previously-identified to be a signal transduction ligand for RAGE (1), or the indicated mediators. Assessment of activation of phosphorylated MEK 1/2 and p44/p42 MAP kinase by immunoblotting or nuclear translocation of NF-kB was performed. All reagents were tested for endotoxin content using the limulus amebocyte assay (Sigma). Any endotoxin identified in these assays was removed by chromatography of the protein solutions onto Detox-igel columns (Pierce, Arlington Hts, Ill.). The material was re-tested in the limulus amebocyte assay for the absence of detectable endotoxin.

Radioligand binding assays. Purified EN-RAGE was radiolabelled using $^{125}$I and Iodobeads (Pierce, Arlington Heights, ILL) to a specific activity of approximately 5,000 cpm/ng. Radioligand binding assays were performed in 96-well tissue culture dishes containing the indicated transfected CHO cells in the presence of the indicated concentration of radiolabelled EN-RAGE±an 50-fold molar excess of unlabelled EN-RAGE in PBS containing calcium/magnesium and BSA, 0.2%, for 3 hrs at 37° C. Wells were washed rapidly with washing buffer (PBS containing Tween 20 (0.05%)). Elution of bound material was performed in a solution containing heparin, 1 mg/ml. The aspirate was counted in a gamma counter (LKB, Gaithersburg, Md.). Equilibrium binding data were analyzed according to the equation of Klotz and Hunston (57): $B=nKA/1+KA$, where B=specifically bound ligand (total binding, wells incubated with tracer alone, minus nonspecific binding, wells incubated with tracer in the presence of excess unlabelled material), n=sites/cell, K=the dissociation constant, and A=free ligand concentration) using nonlinear least-squares analysis (Prism; San Diego, Calif.). Where indicated, pretreatment with antibodies (70 µg/ml), or human soluble RAGE (50-fold molar excess), was performed.

Activation of pMEK 1/2 and p44/p42 MAP kinases. CHO cells were incubated with EN-RAGE, 10 µg/ml, for one hr. Cells were lysed in lysis buffer (New England Biolabs, Beverly, Mass.) and lysate was subjected to centrifugation. Protein concentration of the supernatant was determined by Bio-Rad assay (Bio-Rad, Hercules, Calif.). Equal amounts of protein were subjected to SDS-PAGE (Novex/Invitrogen). Contents of the gels were transferred to nitrocellulose and immunoblotting performed using anti-phosphorylated/total p44/p42 MAP kinase and MEK 1/2 (New England Biolabs) (1 µg/ml).

Electrophoretic mobility shift assay. Nuclear extracts were prepared using the NE kit (Pierce) and EMSA performed employing consensus $^{32}$P-labelled probe for NF-kB as described (1). Where indicated, cells were treated with either nonimmune/anti-RAGE IgG, or soluble RAGE (1,21).

Peripheral Blood-derived Mononuclear Phagocyte (MPs) Studies

Cellular isolation. Venous blood was obtained from healthy volunteers (30 ml) bearing RAGE 82G or 82G/82S in accordance with the policies of Columbia University's Institutional Review Board. Due to the rare numbers of subjects homozygous for the 82S allele, the studies were confined to those bearing solely 82G or heterozygous 82G/82S. Mononuclear cells were isolated using Histopaque 1077 (Sigma, St. Louis, Mo.) and cultured on plastic dishes for 3 hrs at 37° C. Nonadherent cells were removed by washing in PBS. Adherent cells were removed by incubation with EDTA (2 mM) for 15 mins at 37° C. Cells (>95% MPs as assessed by immunostaining with anti-CD68 IgG) were seeded in tissue culture-coated wells for study.

Activation of phosphorylated MEK 1/2 and p44/p42 MAP kinases and generation of IL-6 and TNF-alpha. MPs were seeded onto the wells of 24-well tissue culture plates at a density of $5\times10^5$ cells per well. Cells were stimulated with either BSA or EN-RAGE (10 µg/ml), and immunoblotting for detection of phosphorylated/total MEK 1/2 and p44/p42 MAP kinases performed as above. Supernatant was assayed for IL-6 and TNF-alpha using ELISA kits from R&D systems (Minneapolis, Minn.).

Patient Population and Detection of 82S Polymorphism

RA patients used for association studies meet the criteria of the American College of Rheumatology (58) and were taken from patient populations collected previously at the Medical College of Virginia, Virginia Commonwealth University (31). The following primers were synthesized for detection of the glycine82serine (G82S) polymorphism of the RAGE gene (8): sense primer: 5' GTAAGCGGGGCTCCTGTTGCA-3' (SEQ. ID NO. 1) and the antisense primer: 5' GGCCAAG- GCTGGGGTTGAAGG-3' (SEQ. ID NO. 2). Whole blood (20 μl) was obtained from human volunteers in accordance with the standards and policies of the Institutional Review Boards of the institutions. Genomic DNA was prepared using a kit from Qiagen (Valencia, Calif.); 10 ng was amplified using Taq DNA polymerase (Life Technologies, Grand Island, N.Y.) in a final volume of 25 μl and PCR performed as follows: 94° C. for 30 secs, 62° C. for 45 secs, and 72° C. for 60 secs for a total of 35 cycles. PCR product (25 μl) was digested with Alu I (Life Technologies), 3 U for 16 hr at 37° C., followed by electrophoresis on 2% agarose gels.

Statistical Analysis

Statistical comparisons were determined using one-way analysis of variance (ANOVA); where indicated, individual comparisons were performed using students' t-test. For cell culture studies, immunoblotting, zymography and electrophoretic mobility shift assays were performed at least three times. Statistical analyses were performed across each of the experiments by scanning gels/autoradiograms into a densitometer. Arbitrary units of intensity (Image Quant/Molecular Dynamics (Foster City, Calif.)) were then standardized using untreated cells as control, and assigned a value of "1". Similarly, in animal studies, an arbitrary value of "1" was assigned to bands (immunoblotting or zymography) in assays from animals without collagen-induced arthritis). Statistical analyses to identify the incidence of G82S in human subjects were performed as previously described (59-60). $P<0.05$ was considered statistically significant.

Results

RAGE and Murine Collagen-Induced Arthritis

As a first test of the hypothesis that RAGE contributed to inflammatory and tissue-destructive mechanisms in arthritis, arthritis was induced in DBA/1 mice by sensitization and challenge with bovine type II collagen, the predominant protein of articular cartilage (15-17). Bovine type II collagen was emulsified in complete Freund's adjuvant and injected intradermally at the base of the tail (day 0). Three weeks later, mice were challenged with bovine type II collagen (day 22). The contribution of RAGE to the pathogenesis of arthritis was studied by treating animals with soluble (s) RAGE (1,18), the extracellular ligand-binding domain of the receptor, 100 μg per day, beginning three weeks after initial immunization (day 22). In previous studies, blockade of RAGE at this dose effected the greatest decrease in the proinflammatory phenotype in a murine model of delayed-type hypersensitivity (1).

Figures 1A, 1B, 1C, 1D, 1E, 1F, 1G, 1H, 1I, 1J, 1K, 1L, 1M, 1N:
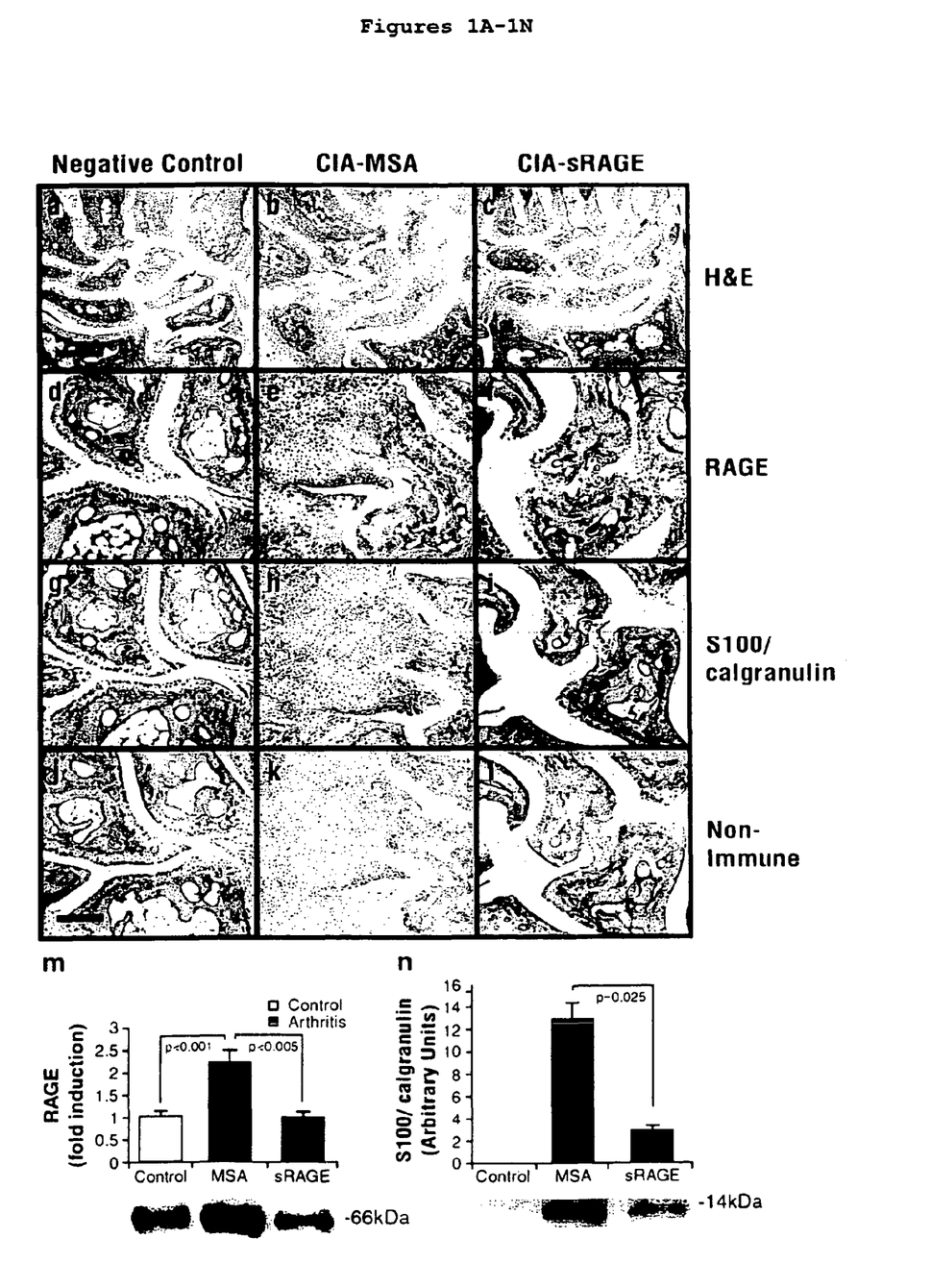

The relevance of RAGE-ligand interaction to murine collagen-induced arthritis was underscored by the increased expression of RAGE and S100/calgranulins in joint tissue. Six weeks after immunization, RAGE and S100/calgranulin expression was increased in joints from mice with arthritis compared with controls, especially within the proliferating synovium (RAGE, FIGS. 1e&d; S100/calgranulin, FIGS. 1h&g, respectively) By immunoblotting, levels of RAGE antigen were enhanced ~2.2-fold in arthritis versus control joints (FIG. 1m). Although levels of S100/calgranulins were quite low in joint tissue of control DBA/1 mice without collagen-induced arthritis, expression of these proinflammatory mediators was induced in murine serum albumin-treated mice immunized/challenged with bovine type II collagen (FIG. 1n). In mice subjected to blockade of RAGE with sRAGE, levels of RAGE and S100/calgranulin antigens by immunoblotting were significantly reduced compared to mice treated with vehicle (FIGS. 1m&n, respectively).

Figure 2A:
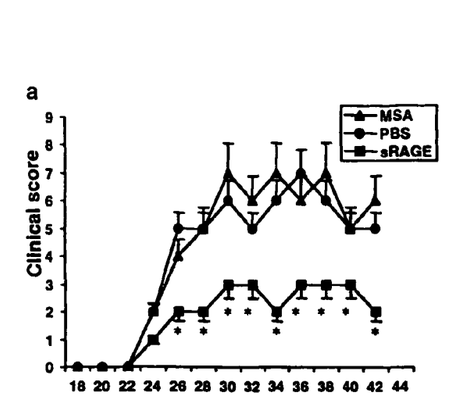
Figure 2B:
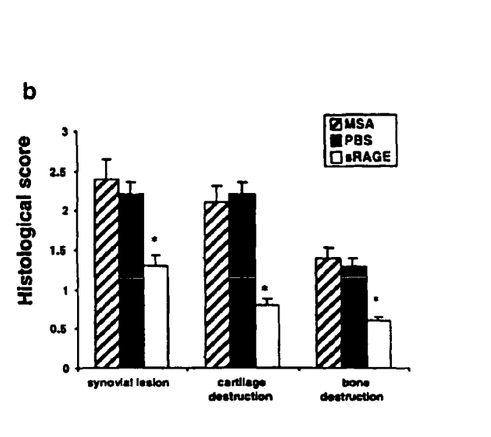
Figure 2C:
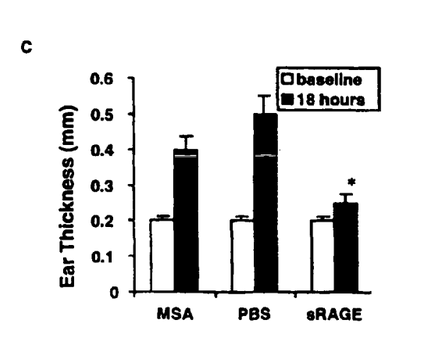
Figure 2D:
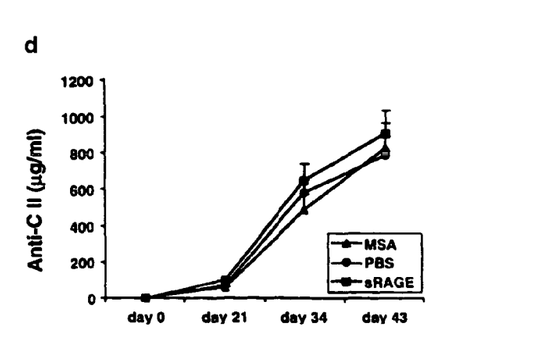

In parallel with reduced expression of RAGE and S100/calgranulins in sRAGE-treated joints, clinical indices of inflammation (18) were consistently lower in mice treated with sRAGE vs PBS or murine serum albumin (FIG. 2a). In addition, histologic scoring (19) revealed marked decreases in synovial hyperplasia/hypertrophy in the joints of sRAGE-treated mice (FIG. 2b). Further, histologic indices of cartilage and bone destruction (20) were significantly decreased in sRAGE-treated mice compared with those animals receiving PBS or murine serum albumin (FIG. 2b) To determine if blockade of RAGE suppressed immune/inflammatory responses to bovine type II collagen at extra-articular sites, mice receiving vehicle or sRAGE were injected with bovine type II collagen (10 μg) into ear tissue six weeks after immunization (day 42). Although baseline ear thickness was identical in all groups, 18 hrs after injection of collagen, mice receiving murine serum albumin or PBS revealed significant increases in ear thickness compared with those mice treated with sRAGE (FIG. 2c). Levels of serum total IgG developed against bovine type II collagen were unchanged in the presence of sRAGE vs PBS or murine serum albumin, thereby indicating that blockade of RAGE did not suppress primary immunization (FIG. 2d).

Figure 3A:
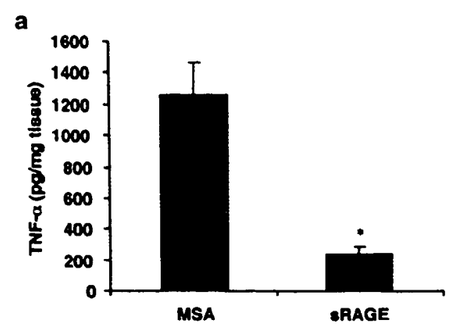
Figure 3B:
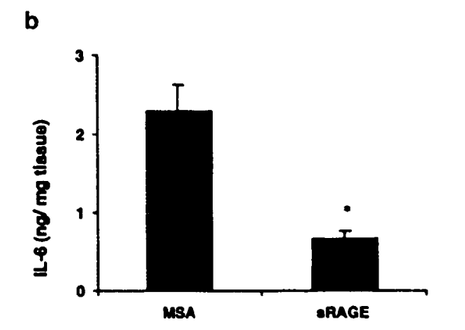
Figure 3C:
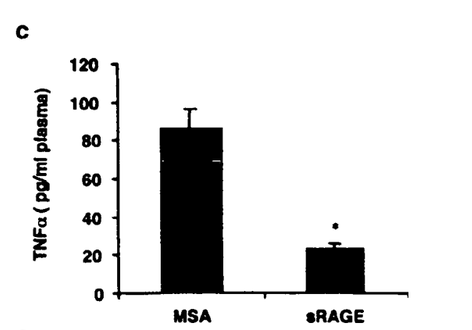
Figure 3D:
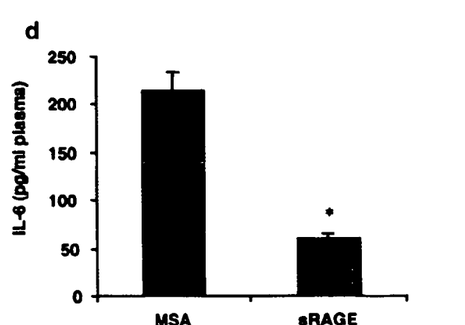

To dissect the molecular mechanisms underlying the protection afforded by RAGE blockade, levels of cytokines and matrix metalloproteinases (MMPs) in the tissues were assessed. ELISA on extracts prepared from stifle joints revealed a significant reduction in levels of TNF-alpha (~4.3-fold) and IL-6 (~3.1-fold) from mice immunized with bovine type II collagen treated with sRAGE vs murine serum albumin (FIGS. 3a&b, respectively). Similarly, levels of plasma TNF-alpha and IL-6 antigens were significantly reduced, ~3.5- and 3.6-fold, in sRAGE-treated mice compared with those animals receiving murine serum albumin (FIGS. 3c&d, respectively).

Figure 3E:
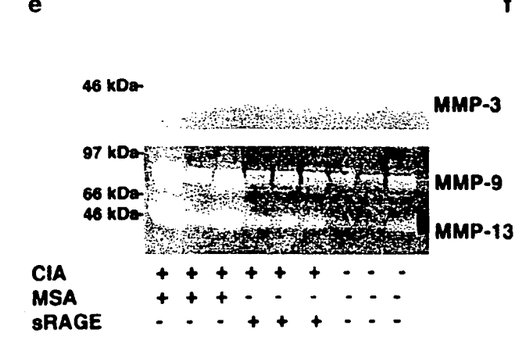
Figure 3F:
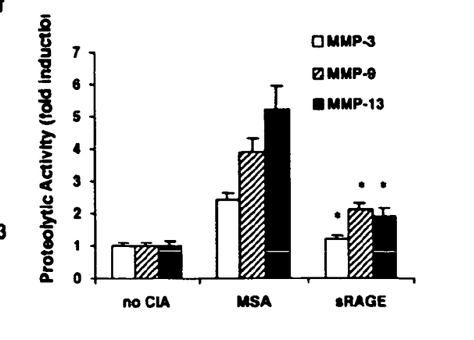

As induction of TNF-alpha and other inflammatory cytokines sets in motion events leading to activation of latent/proenzyme MMPs (21), activity of MMPs 3, 9 and 13 in joint tissue was assessed. Compared with control joints, tissue retrieved from murine serum albumin-treated mice undergoing the collagen-induced arthritis protocol revealed an ~2.5-fold, ~4.0-fold and ~5.3-fold increase in activity of MMPs 3, 9 and. 13, respectively, by zymography (FIGS. 3e&f). That activation of RAGE was critical in this process was demonstrated by the significant reduction in activation of these MMPs in joint tissue of sRAGE-treated mice (FIGS. 3e&f, respectively).

Taken together, these observations suggested that interaction of S100/calgranulins and RAGE, both enriched in joint tissues in arthritis, activates proinflammatory and tissue-destructive mediators, thereby supporting roles for these molecules in the evolution of joint destruction.

Figure 4A:
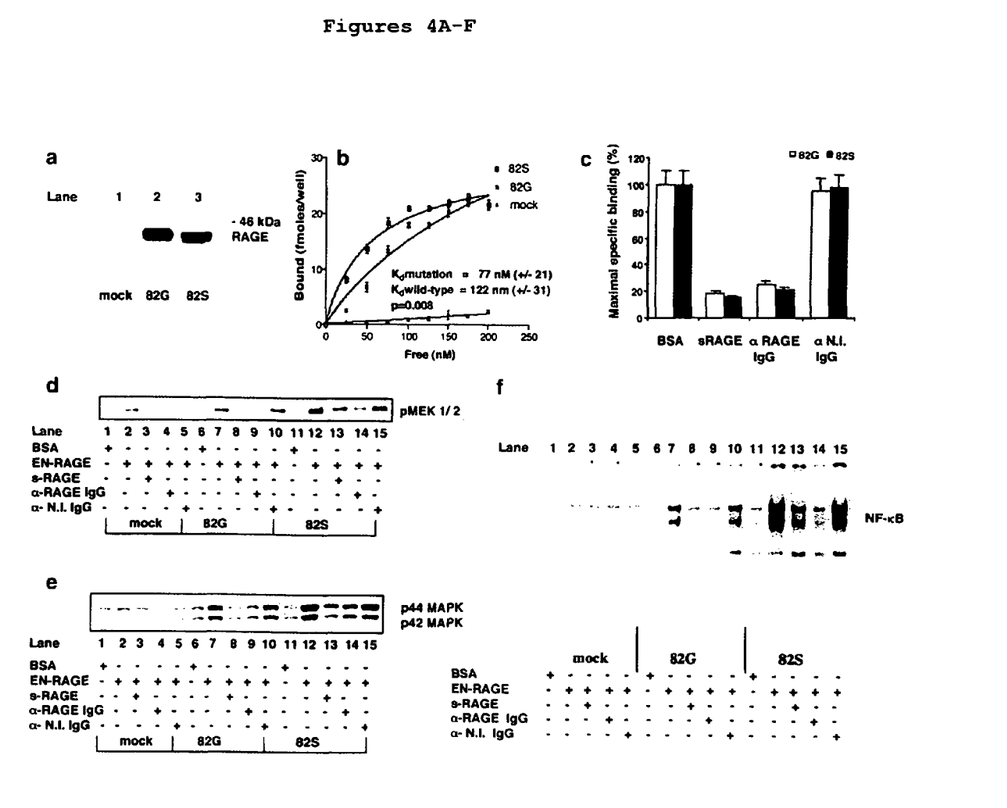

RAGE 82S Allele Enhances Binding/Signalling/Gene Expression by S100/Calgranulins Polymorphisms within the RAGE gene may influence these effects by altering proinflammatory pathways. To study this, whether the glycine to serine polymorphism (G82S) within the ligand-binding domain of RAGE displayed enhanced ligand affinity and activation of signal transduction pathways was tested. Stably-transfected Chinese hamster ovary (CHO) cells bearing the two RAGE alleles of interest were prepared, either the common RAGE 82G allele, or the variant RAGE 82S allele. CHO cells provide a convenient model, as they are devoid of detectable RAGE prior to (not shown), or after stable transfection with pcDNA3.1 vector alone (mock) (FIG. 4a). Stably-transfected CHO cells were made with pcDNA3.1 containing either RAGE 82G or RAGE 82S (FIG. 4a). ELISA studies demonstrated that levels of RAGE antigen were identical in both CHO cells transfected to express RAGE 82G or RAGE 82S (data not shown). Radio-ligand binding studies showed dose-dependent binding of $^{125}$I-EN-RAGE (a prototypic S100/calgranulin) to CHO cells expressing RAGE 82G (~122±31 nM) and 82S receptor (Kd ~77±21 nM), though the affinity of binding was greater with the 82S allele (p=0.008; FIG. 4b). In contrast, CHO cells stably transfected with the empty vector displayed no specific binding of $^{125}$I-EN-RAGE (FIG. 4b). That the interaction of RAGE-bearing CHO cells with $^{125}$I-EN-RAGE was specific for interaction with RAGE was shown by suppression of specific binding in the presence of excess soluble extracellular domain of the receptor (sRAGE), or anti-RAGE IgG, but not by bovine serum albumin (BSA) or nonimmune IgG (FIG. 4c).

These observations led to testing the concept that the 82S RAGE isoform might amplify cellular activation beyond that seen in cells bearing wild-type RAGE. Incubation of mock-transfected CHO cells with a physiologically-relevant concentration of EN-RAGE (4), 10 μg/ml, did not significantly increase intensity of the bands corresponding to phosphorylated MEK 1/2 or p44/42 MAP kinases (22-23) (FIGS. 4d&e, respectively; lanes 1-5). However, exposure of RAGE 82G CHO transfectants to EN-RAGE increased by ~2.2-fold and ~1.9-fold phosphorylated MEK 1/2' and p44/42 MAP kinases, compared with cultures incubated with BSA alone (p<0.01; FIGS. 4d&e, respectively; lanes 7&6). CHO transfectants bearing RAGE 82S incubated with EN-RAGE displayed ~3.6-fold and ~4.1-fold increase in phosphorylated MEK 1/2 and p44/42 compared with BSA (p<0.01; FIGS. 4d&e, respectively; lanes 12&11). Thus, compared with cells expressing the common RAGE 82G allele, CHO cells expressing the variant RAGE 82S displayed significantly increased phosphorylation of MEK 1/2 and p44/p42 MAP kinases by $^{18}$ 1.6- and ~2.2-fold (p<0.05; FIGS. 4d&e, respectively; lanes 12&7). In both RAGE 82G and RAGE 82S-transfected cells, cellular activation by EN-RAGE was due to engagement of RAGE as demonstrated by suppression of phosphorylation of MEK 1/2 and p44/p42 by excess sRAGE (FIGS. 4d&e, respectively; lanes 8&13), or anti-RAGE IgG (FIGS. 4d&e, respectively, lanes 9&14). Nonimmune IgG was without effect (FIGS. 4d&e, respectively; lanes 10&15). In each case, respective levels of total MEK 1/2 and p44/p42 MAP kinases were identical (data not shown).

To further support the hypothesis that RAGE 82S enhanced activation of key proinflammatory signal transduction pathways, nuclear translocation of NF-kB in CHO transfectants exposed to EN-RAGE were assessed. Electrophoretic mobility shift assays (EMSA) using $^{32}$P-labelled consensus NF-kB probe and nuclear extracts from mock-transfected CHO cells showed no increase in intensity of the gel shift band after cultures were exposed to EN-RAGE (FIG. 4f, lane 2). In CHO transfectants expressing RAGE 82G, there was a prominent ~2.4-fold increase in intensity in nuclear binding activity following incubation of cultures with EN-RAGE compared to BSA (p<0.05; FIG. 4f, lanes 7&6, respectively). NF-kB activation was even more striking when RAGE 82S was substituted for RAGE 82G. RAGE 82S CHO transfectants displayed ~5.1-fold increased intensity of the gel shift band consequent to the presence of EN-RAGE, compared to incubation with BSA (p<0.001; FIG. 4f, lanes 12&11, respectively). Thus, RAGE-mediated NF-kB activation due to EN-RAGE was significantly enhanced by ~2.1-fold comparing RAGE 82S to 82G; p<0.01. That activation of NF-kB in transfected CHO cells by EN-RAGE resulted from ligation of common or variant RAGE was confirmed by its suppression in the presence of sRAGE (FIG. 4f, lanes 8&13, respectively), or anti-RAGE IgG (FIG. 4f, lanes 9&14, respect-ively), but not by nonimmune IgG (FIG. 4f, lanes 10&15, respectively).

Figure 5A:
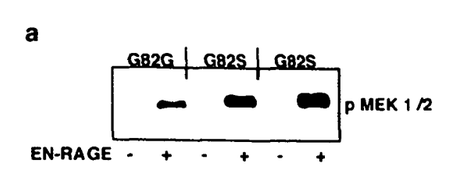
Figure 5B:
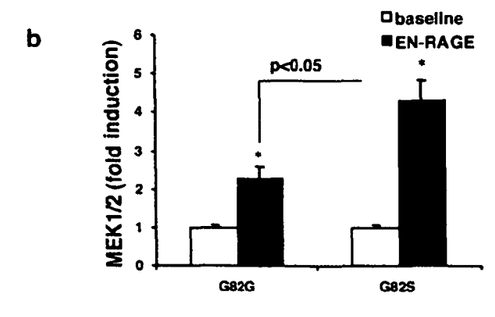
Figure 5C:
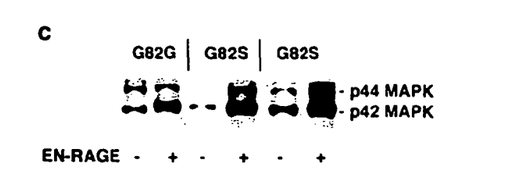
Figure 5D:
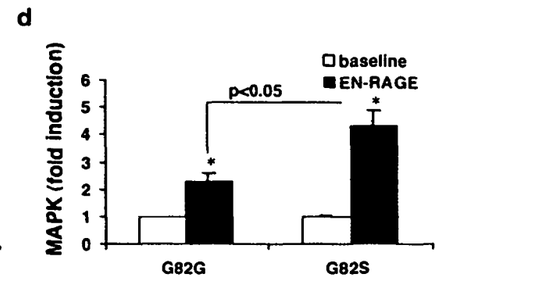

A critical test of the concept that S100/calgranulin-RAGE 82S interaction might enhance proinflammatory effects was whether mononuclear phagocytes (MPs) retrieved from human subjects bearing the variant RAGE 82S allele displayed heightened activation of signal transduction molecules in the presence of ligand. Due to the rare number of subjects homozygous for 82S in our study populations, studies were limited to those individuals homozygous for the common RAGE allele 82G, or those subjects heterozygous for 82G and 82S alleles. ELISA revealed that basal levels of RAGE antigen did not differ between MPs bearing 82G or 82G/82S (data not shown). Signalling was compared in MPs from subjects bearing RAGE 82G and RAGE 82G/82S by assessing activation of MEK 1/2 and p44/p42 MAP kinases. In the presence of EN-RAGE, MPs isolated from individuals bearing RAGE 82G/82S displayed an ~4.5- and 4.3-fold increase in phosphorylated MEK 1/2 and p44 and p42 MAP kinases, respectively, compared with unstimulated cells (p<0.01; FIGS. 5a,b,c&d). However, MPs bearing the common RAGE 82G allele exposed to EN-RAGE revealed a significant, although smaller ($^{18}$ 2.6- and 2.3-fold) increase in activation of MEK 1/2 and p44/p42 MAP kinases, respectively (p<0.01; FIGS. 5a,b,c&d). Importantly, EN-RAGE-triggered activation of MEK 1/2 and p44/p42 MAP kinases was significantly increased in heterozygous RAGE 82G/82S-bearing MPs vs those MPs expressing RAGE 82G (p<0.05; FIGS. 5b&d).

Figure 5E:
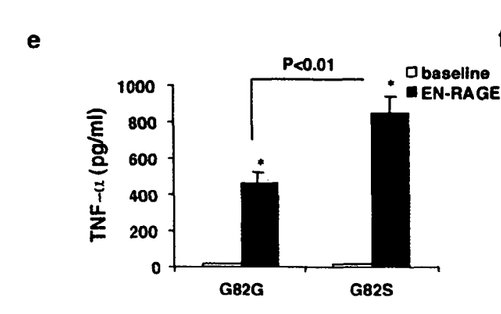
Figure 5F:
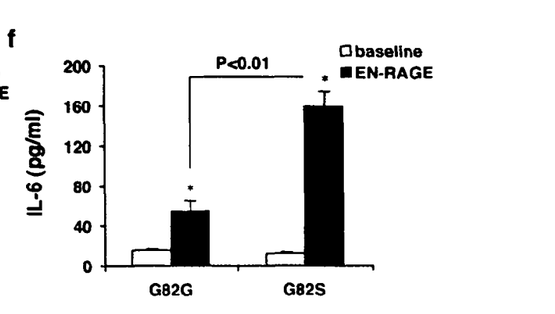

To assess the functional consequences of enhanced binding and activation of signal transduction molecules stimulated upon ligation of RAGE by EN-RAGE, production of key inflammatory and tissue-degradative mediators linked to RA (24-26) by MPs bearing common or variant RAGE alleles were examined. Exposure of RAGE 82G-bearing MPs to EN-RAGE caused a significant increase in generation of TNF-alpha detected in culture supernatant compared with quiescent cultures (470±53 vs 15±2 pg/ml; p<0.001) (FIG. 5e). However, upon incubation of human MPs bearing RAGE 82G/82S, an even greater increase in elaborated TNF-alpha was observed in culture supernatants compared to basal levels (850±64 vs 17±2 pg/ml; p<0.01) (FIG. 5e). Importantly, although basal levels of TNF-alpha did not differ between RAGE 82G and 82G/82S-bearing MPs, levels of TNF-alpha in EN-RAGE-stimulated MPs were increased ~1.8-fold in the presence of RAGE 82G/82S compared with RAGE 82G (p<0.01; FIG. 5e). Similarly, RAGE 82G-bearing MPs exposed to EN-RAGE displayed a small, but significant increase in generation of IL-6 compared with basal expression (55±7 vs 15±2 pg/ml; p<0.01) (FIG. 5f). However, MPs bearing. RAGE 82G/82S revealed augmented generation of IL-6 upon incubation with EN-RAGE compared with unstimulated controls (160±14 vs 12±2 pg/ml; p<0.01) (FIG. 5f). EN-RAGE-stimulated MPs bearing RAGE 82G/82S generated increased amounts of IL-6 compared with cells from subjects bearing RAGE 82G (~2.9-fold) (p<0.01; FIG. 5f).

Figure 5G:
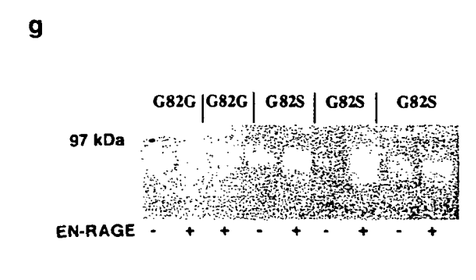
Figure 5H:
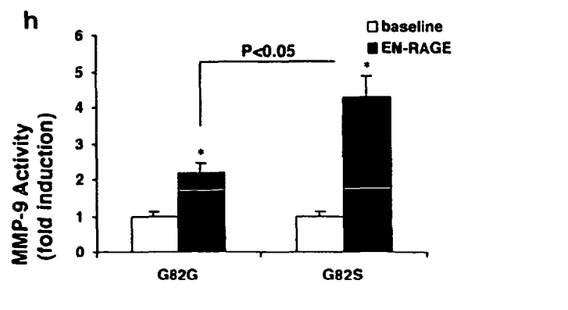

A central means by which structural elements of joints are degraded in unchecked RA is by generation of MMPs, such as MMP-9 (27-30). It was hypothesized that RAGE-mediated MP activation would augment generation of MMP activity on cells bearing RAGE 82G/82S versus RAGE 82G. Activity of MMP-9 in MPs retrieved from subjects bearing the common or variant RAGE alleles was tested. MPs from subjects bearing RAGE 82G displayed an ~2.3-fold increase in MMP-9 activity in the presence of EN-RAGE compared with basal expression (p<0.01; FIGS. 5g&h). However, MPs isolated from individuals bearing RAGE 82G/82S demonstrated an ~4.3-fold increase in EN-RAGE-mediated MMP-9 activity compared with baseline (p<0.01; FIGS. 5g&h). Although basal levels of MMP-9 activity did not differ among 82G- or 82G/82S-bearing MPs, the extent of EN-RAGE-mediated enhanced MMP-9 activity was significantly enhanced, ~1.9-fold, in MPs bearing RAGE 82G/82S vs RAGE 82G (p<0.05; FIGS. 5g&h).

Taken together, the studies in DBA/1 mice suggest that activation of RAGE amplifies cytokine generation and activation of MMPs in joint tissue primed by immunization with bovine type II collagen. These considerations, together with the findings in vitro suggesting that S100/calgranulin-RAGE interaction modifies cellular responses, especially in the presence of the 82S allele, led to the evaluation of the association of the RAGE 82S allele with RA.

RAGE 82S Allele and Association with Rheumatoid Arthritis

Subjects from a previously-reported Caucasian population of RA patients (n=205) and matched controls (n=169) (31) were evaluated. The RAGE 82S allele exhibited an association with RA with relative risk (RR)=2.6, p<0.001 (table 1a). Further analyses were performed to account for the linkage disequilibrium described previously between RAGE 82S and an RA-associated allele, HLA-DRB*0401 (9,32-34). To assess whether the RAGE 82S allele confers risk independent of DRB1*0401, the frequency of the RAGE 82S allele in 0401+ patients and controls was compared. This analysis did not reveal a significant independent effect of RAGE 82S on RA disease susceptibility; p=0.13 by Fisher's exact test (table 1b). However, DRB1*0401 continued to exhibit a significant association with RA in the absence of the RAGE 82S allele (table 1c).

Discussion

S10/calgranulin molecules have been extensively linked to immune/inflammatory diseases. Although their intracellular functions are relatively well-defined, such as calcium-dependent chemotaxis, degranulation and phagocytosis by activated granulocytes (5-6,35), an increasingly recognized view is that these molecules may exhibit distinct functions in the extracellular milieu (35). These concepts are consistent with the observations that the degree of elevation of S100/calgranulins in inflamed foci may mirror the extent of disease activity. For example, in addition to their association with disease severity in RA (4), S100/calgranulins have been linked to disease progression in inflammatory bowel disease (36,37) Furthermore, strongly increased expression of a member of this family of molecules, psoriasin, has been demonstrated in psoriatic lesions compared with adjacent unaffected skin in human subjects (38), thus further supporting the premise that S100/calgranulins may not simply be "innocent bystanders," but, rather, by virtue of their engagement of RAGE (1), active participants in the host inflammatory response. One can speculate that triggered by interaction with accumulating S100/calgranulins, activation of RAGE engages key signalling pathways linked to proinflammatory responses, such as MAP kinases and NF-kB, thereby amplifying expression of molecules linked to chronic cellular perturbation and tissue destruction. This hypothesis appears to be supported by the studies in DBA/1 mice immunized/challenged with bovine type II collagen, as activation of RAGE mediated, at least in part, increased generation of inflammatory cytokines and activation of MMPs. Indeed, blockade of the receptor was associated with decreased clinical and histologic indices of inflammation and bone/cartilage destruction in this model.

Polymorphic differences in the RAGE gene may lead to varied effects of RAGE in inflammatory settings. This led to the investigation of the effects of the G82S polymorphism in the binding domain of RAGE on receptor function and on the inflammatory response. In transfected CHO cells, increased ligand affinity was found to be conferred by the 82S isoform, which, upon further analysis, demonstrated upregulation of intracellular signalling pathways linked to modulation of proinflammatory genes upon interaction with S100/calgranulin. Using isolated MPs from human subjects, significant differences in inflammatory responses between cells isolated from homozygous wild-type G82G and heterozygous G82S subjects were demonstrated. These effects were quite marked between wild-type and heterozygote subjects, thereby suggesting that the 82S allele alone may impart an even greater effect.

Finally, the prevalence of the 82S allele in a population of subjects with RA was investigated. The results demonstrated a statistically-significant increase in prevalence of the 82S allele in subjects with RA. Sub-analysis for the presence/absence of DRB1*0401 led to the loss of an statistically-significant association of 82S with RA (p=0.13 despite odds ratio 3.2). Conversely, DRB1*0401 continued to exhibit a significant association with RA in the absence of the RAGE 82S allele. Clearly, the large genetic susceptibility to RA related to the MHC (39-40) cannot be ascribed solely to the RAGE 82S allele. Due to the relatively low frequency of the 82S allele and low subject numbers in these Caucasian cases and controls after sub-analysis, it remains possible that the RAGE G82S polymorphism is related independently to RA.

The literature is conflicting with respect to a role for DR4 haplotypes in disease severity (41-50). In view of the linkage disequilibrium between DRB1*0401 and the RAGE 82S allele, it will be interesting to specifically test whether DR4 haplotypes containing the RAGE 82S allele have an influence on disease progression and outcome. By analogy with the observations in cultured CHO and human mononuclear cells, one can speculate it may be possible to identify a subset of subjects with RA particularly vulnerable to the sequelae of heightened production/activation of proinflammatory mediators. Specifically, in parallel with outcome measures of clinical severity, such as numbers of bony erosions, the extent of elevation of TNF-alpha, IL-6 and MMP activities in rheumatoid joint fluid and/or RA plasma must be correlated with subject genotype.

A general implication of these studies is that the classical DRB1 associations with RA may not completely explain the underlying reasons for the strong linkage and association of the MHC with RA. Indeed, a number of recent reports indicate that additional genes in the TNF region may influence disease susceptibility, independent of DRB1, and unrelated to DR4 haplotypes (51-52). A full understanding of the role of the MHC in RA and other autoimmune diseases will require a more detailed analysis of this genetic region, since there are many genes within the MHC, in addition to RAGE, which may influence the immune/inflammatory response (53).

Lastly, in addition to the 82S variant of the RAGE gene, it will be important to examine the potential role of other variants of RAGE in disease susceptibility and/or severity in immune/inflammatory diseases. In this context, recently identified polymorphisms within the promoter of the gene encoding RAGE may hold the key to unique elements controlling enhanced transcription of the RAGE gene and increased expression of cell surface RAGE (54). As a number of studies have suggested that expression of RAGE is increased at sites of ligand accumulation such as diabetic atherosclerotic lesions, infected periodontium or Alzheimer disease brain (13,18,55), polymorphisms within regulation elements and/or ligand-binding regions may, alone or in combination, orchestrate RAGE's availability and/or functional potential in a given milieu (56).

In conclusion, one can propose that these observations in an animal model of inflammatory arthritis and in S100/calgranulin-stimulated activation of 82S RAGE-bearing cells highlight ligand-RAGE engagement as an amplifier of proinflammatory mechanisms in immune/inflammatory diseases. These findings provide a compelling rationale to expand the analysis of RAGE polymorphisms and investigate their potential contribution to susceptibility and/or progression of the inflammatory response in diverse diseases with an immune/inflammatory component, such as RA, atherosclerosis and diabetes.

REFERENCES

1. Hofmann M A, Drury S, Fu C, et. al. RAGE mediates a novel proinflammatory axis: a central cell surface receptor for S100/calgranulin polypeptides. *Cell* 1999; 97: 889-901.
2. Chilosi M, Mombello A, Montagna L, et al. Multimarker immunohistochemical staining of calgranulin, chloroacetate esterase, and S100 for simultaneous demonstration of inflammatory cells on paraffin sections. *J Histochem Cytochem* 1990; 38: 1669-1675.
3. Youssef P, Roth J, Frosch M P et al. Expression of myeloid related proteins (MRP) 8 and 14 and the MRP8/14 heterodimer in rheumatoid arthritis synovial membrane. *J Rheumatol* 0.1990; 26: 2523-2528.
4. Frosch M, Strey A, Vogl T, et al. Myeloid-related proteins 8 and 14 are specifically secreted during interaction of phagocytes and activated endothelium and are useful markers for monitoring disease activity in pauciarticular-onset juvenile rheumatoid arthritis. *Arthritis Rheum* 2000; 43: 628-637.
5. Zimmer D B, Cornwall E H, Landar A, Song W. The S100 protein family: history, function, and expression. *Brain Research Bulletin* 1995; 37: 417-429.
6. Schafer B W, Heinzmann C W. The S100 family of EF-hand calcium-binding proteins: functions and pathology. *TIBS* 1996; 21: 134-140.
7. Rammes A, Roth J, Goebeler M, Klempt M, Hartmann M, Sorg C. Myeloid-related protein (MRP) 8 and MRP14, calcium-binding proteins of the S100 family, are secreted by activated monocytes via a novel, tubulin-dependent pathway. *J Biol Chem* 1997; 272: 9496-9502.
8. Hudson B I, Stickland M H, Grant P J. Identification of polymorphisms in the Receptor for Advanced Glycation End Products (RAGE) gene. *Diabetes* 1998; 47: 1155-1157.
9. Prevost G, Fajardy I, Fontaine P, Danze P M, Besmond C. Human RAGE Gly82Ser dimorphism and HLA class II DRB1-DQA1-DQB1 haplotypes in type 1 diabetes. *Europ J Immunogenet* 1999; 26: 343-348.
10. Neeper M, Schmidt A M, Brett J, et al. Cloning and expression of RAGE: a cell surface receptor for advanced glycosylation end products of proteins. *J. Biol. Chem.* 1992; 267: 14998-15004.
11. Schmidt A M, Vianna M, Gerlach M, et al. Isolation and characterization of binding proteins for advanced glycosylation endproducts from lung tissue which are present on the endothelial cell surface. *J. Biol. Chem.* 1992; 267: 14987-14997.
12. Kislinger T, Fu C, Huber B, et al. $N^\epsilon$ (carboxymethyl) lysine adducts of proteins are ligands for receptor for advanced glycation endproducts that activate cell signaling pathways and modulate gene expression. *J Biol Chem* 1999; 274: 31740-31749.
13. Yan S D, Chen X, Fu J, et al. RAGE and amyloid beta peptide neurotoxicity in Alzheimer's disease. *Nature* 1996; 382: 685-691.
14. Hori O, Brett J, Slattery T. et al. The receptor for advanced glycation endproducts. (RAGE) is a cellular binding site for amphoterin: mediation of neurite outgrowth and coexpression of RAGE and amphoterin in the developing nervous system. *J. Biol. Chem* 1995; 270: 25752-25761.
15. Courtenay J S, Dallman M J, Dayan A D, Martin A, Mosedale B. Immunization against heterologous type II collagen induces arthritis in mice. *Nature* 1980; 283: 666-668.
16. Trentham D E, Townes A S, Kang A H. Autoimmunity to type II collagen an experimental model of arthritis. *J Exp Med* 1997; 146: 857-868.
17. Cathcart E S, Hayes K C, Gonnerman W A, Lazzari A A, Franzblau C. Experimental arthritis in a nonhuman primate. I. Induction by bovine type II collagen. *Lab Invest* 1986; 54: 26-31.
18. Park L, Raman K G, Lee K J, et al. Suppression of accelerated diabetic atherosclerosis by soluble Receptor for AGE (sRAGE). *Nature Medicine* 1998; 4: 1025-1031.
19. Quattrocchi E, Walmsley M, Browne K, et al. Paradoxical effects of adenovirus-mediated blockade of TNF activity in murine collagen-induced arthritis. *J Immunol* 1999; 163: 1000-1009.
20. Neurath M F, Hildner K, Becker C, et al. Methotrexate specifically modulates cytokine production by T cells and macrophages in murine collagen-induced arthritis (CIA): a mechanism for methotrexate-mediated immunosuppression. *Clin Exp Immunol* 1999; 115: 42-55.
21. Pugin J, Widmer M C, Kosodo S, Liang C M, Preas H L II, Suffredini A F. Human neutrophils secrete gelatinase B in vitro and in vivo in response to endotoxin and proinflammatory mediators. *Am J Respir Cell Mol Biol* 1999; 20: 458-464.
22. Lander H L, Tauras J M, Ogiste J S, Moss R A, Schmidt A M. Activation of the Receptor for Advanced Glycation Endproducts triggers a MAP Kinase pathway regulated by oxidant stress. *J. Biol. Chem.* 1997; 272: 17810-17814.
23. Taguchi A, Blood D C, del Toro G A, et al. Blockade of amphoterin/RAGE signalling suppresses tumor growth and metastases. *Nature* 2000; 405: 354-360.
24. Pisetsky D S. Tumor necrosis factor blockers in rheumatoid arthritis. *N Engl J Med* 2000; 342: 810-811.
25. Boe A, Baiocchi M, Carbonatto M, Papoian R, Serlupi-Crescenzi O. Interleukin-6 knock-out mice are resistant to antigen-induced experimental arthritis. *Cytokine* 1999; 11: 1057-1064.
26. Robak. T, Gladalska A, Stepien H, Robak E. Serum levels of interleukin-6 type cytokines and soluble interleukin-6 receptor in patients with rheumatoid arthritis. *Mediators Inflamm* 1998; 7: 347-353.
27. Keyszer G, Lambiri I, Nagel R, et al. Circulating levels of matrix metalloproteinases MMP-3 and MMP-1, tissue inhibitor of metalloproteinases 1 (TIMP-1), and MMP-1/TIMP-1 complex in rheumatic disease. Correlation with clinical activity of rheumatoid arthritis versus other surrogate markers. *J Rheumatol* 1999; 26: 251-258.
28. Konttinen Y T, Ainola M, Valleala H, et al. Analysis of 16 different matrix metalloproteinases (MMP-1 to MMP-20) in the synovial membrane: different profiles in trauma and rheumatoid arthritis. *Ann Rheum Dis* 1999; 58: 691-697.
29. Iwaki-Egawa S, Watanabe Y, Matsuno H. Correlations between matrix metalloproteinase-9 and adenosine deaminase isozymes in synovial fluid from patients with rheumatoid arthritis. *J Rheumatol* 2001; 28: 485-489.

30. Kaneko O, Tomita. T, Nakase T, et al. Expression of proteinases and inflammatory cytokines in subchondral bone regions in the destructive joint of rheumatoid arthritis. *Rheumatology* 2001; 40: 247-255.
31. Meyer J M, Han J, Singh R, Moxley G. Sex influences on the penetrance of HLA shared-epitope genotypes for rheumatoid arthritis. *Am J Hum Genet* 1996; 58: 371-383.
32. Gregersen P K, Silver J, Winchester R J. The shared epitope hypothesis. An approach to understanding the molecular genetics of susceptibility to rheumatoid arthritis. *Arthritis Rheum* 1987; 30: 1205-1213.
33. Stastny P. Association of the B-cell autoantigen DRW4 with rheumatoid arthritis. *N Engl J Med* 1978; 298: 869-871.
34. Sugaya K, Fukagawa T, Matsumoto K, et al. Three genes in the MHC Class III region near the junction with the class II: gene for Receptor of Advanced Glycosylation End Products, PBX2 homeobox gene and a notch homolog, human counterpart of mouse mammary tumor gene int-3. *Genomics,* 1994; 23: 408-419.
35. Donato R. S100: a multigenic family of calcium-modulated proteins of the EF-hand type with intracellular and extracellular functional roles. *Intl J Biochem Cell Biol* 2001; 33: 637-668.
36. Lugering N, Stoll R, Schmid K W, et al. The myeloic related protein MRP8/14 (27E10 antigen)-usefulness as a potential marker for disease activity in ulcerative colitis and putative biological function. *Europ. J Clin Invest* 1995; 25: 659-664.
37. Schmid K W, Lugering N, Stoll R, et al Immunohistochemical demonstration of calcium-binding proteins MRP8 and MRP 0.14 and their heterodimer (27E10 antigen) in Crohn's disease. *Human Pathol* 1995; 26: 334-337.
38. Madsen P. Molecular cloning, occurrence and expression of a novel partially secreted protein "psoriasin" that is highly up-regulated in psoriatic skin. *J Invest Dermatol* 1991; 97: 701-7.12.
39. Gregersen P K. The North American Rheumatoid Arthritis Consortium—bringing genetic analysis to bear on disease susceptibility, severity and outcome. *Arthritis Care* 1998; 11: 1-2.
40. Cornelis F, Faure S, Martinez M, et al New susceptibility locus for rheumatoid arthritis suggested by a genome-wide linkage study. *Proc Natl Acad Sci USA* 1998; 95:10746-10750.
41. Weyand C M, Hicok K C, Conn D L, Goronzy, J. J. The influence of HLA-DRB1 genes on disease severity in rheumatoid arthritis. *Ann Int Med* 1992;117: 801-806.
42. Eberhardt K, Fex E, Johnson U, Wollheim F A. Associations of HLA-DRB and -DQB genes with two and five year outcomes in rheumatoid arthritis. *Ann Rheum Dis* 1996; 55: 34-39.
43. Reveille J D, Alarcon G S, Fowler S E, et al HLA-DRB1 genes and disease severity in rheumatoid arthritis. *Arthritis Rheum* 1996; 39: 1802-1807.
44. Criswell L A, Mu H, Such C L, King M C. Inheritance of the shared epitope and long-term outcomes of rheumatoid arthritis among community-based Caucasian females. *Genet Epidemiol* 1998; 15: 61-72.
45. Weyand C M, McCarthy T G, Goronzy J J. Correlation between disease phenotype and genetic heterogeneity in rheumatoid arthritis. *J Clin Invest* 1995; 95: 2120-2126.
46. Hall F C, Weeks D E, Camillieri J P, et al Influence of the HLA-DRB1 locus on susceptibility and severity in rheumatoid arthritis. *QJM* 1996; 89: 821-829.
47. Mattey D L, Hassell A B, Plant M J, et al The influence of HLA-DRB1 alleles encoding the DERAA amino acid motif on radiological outcome in rheumatoid arthritis. *Rheumatology (Oxford)* 1999; 38: 1221-1227.
48. Seitz M, Perler M, Pichler W. Only weak association between disease severity and HLA-DRB1 genes in a Swiss population of rheumatoid arthritis patients. *Rheumatol Int* 1996; 16: 9-13.
49. Suarez-Almazor M E, Tao S, Moustarah F, Russell A S, Maksymowych W. HLA-DR1, DR4, and DRB1 disease related subtypes in rheumatoid arthritis. Association with susceptibility but not severity in a city-wide community based study. *J Rheumatol.* 1995; 22: 2027-2033.
50. Harrison B, Thomson W, Symmons D, et al The influence of HLA-DRB1 alleles and rheumatoid arthritis on disease outcome in an inception cohort of patients with early inflammatory arthritis. *Arthritis Rheum* 1999; 42: 2174-2183.
51. Mulcahy B, Waldron-Lynch F., McDermott M F, et al. Genetic variability in the tumor necrosis factor-lymphtoxin region influences susceptibility to rheumatoid arthritis. *Am J Hum Genet* 1996; 59: 676-683.
52. Ota M, Katsuyama Y, Kimura A, et al A second susceptibility gene for developing rheumatoid arthritis in the human MHC is localized within a 70-kb interval telomeric of the TNF genes in the HLA class III region. *Genomics* 2001; 71: 263-270.
53. Complete sequencing and gene map of a human major histocompatibility complex. The MHC sequencing consortium. *Nature* 1999; 401: 921-923.
54. Hudson B I, Stickland M H, Futers T S, Grant P J. Effects of novel polymorphisms in the RAGE gene on transcriptional regulation and their association with diabetic retinopathy. *Diabetes* 2001; 50: 1505-1511.
55. Lalla E, Lamster I B, Feit M, et al Blockade of RAGE suppresses periodontitis-associated alveolar bone loss in diabetic mice. *J. Clin. Invest.* 2000; 105: 1117-1124.
56. Kankova K, Zahejsky J, Marova I, et al. Polymorphisms in the RAGE gene influence susceptibility to diabetes-associated microvascular dermatoses in NIDDM. *J Diabetes Complications* 0.2001; 15: 185-192.
57. Klotz I, Hunston D. Mathematical models for ligand-receptor binding. *J Biol Chem* 1984; 259: 10060-10062.
58. Arnett F C, Edworthy S M, Bloch D A, et al The American Rheumatism Association 1987 revised criteria for the classification of rheumatoid arthritis. *Arthritis Rheum* 1988; 31: 315-324.
59. Svejgaard A, Ryder L P. HLA and disease associations: detecting the strongest association. *Tissue Antigens* 1994; 43: 18-27.1
60. Tiwari J L, Terasaki P I. The data and statistical analysis. In: Tiwari J L, Terasaki PI (eds). *HLA and Disease Associations*. Springer-Verlag, New York, 1985, pp 18-22.
61. U.S. Pat. No. 6,677,299, issued Jan. 13, 2004.
62. U.S. Pat. No. 6,555,651, issued Apr. 29, 2003.
63. U.S. Pat. No. 6,465,422, issued Oct. 15, 2002.
64. U.S. Pat. No. 6,697,669, issued Feb. 24, 2004.
65. U.S. Pat. No. 6,692,966, issued Feb. 17, 2004.
66. U.S. Pat. No. 6,503,887, issued Jan. 17, 2003.
67. U.S. Pat. No. 6,071,890, issued Jun. 6, 2000.
68. U.S. Pat. No. 5,741,486, issued Apr. 21, 1998.
69. U.S. Pat. No. 6,271,210, issued Aug. 7, 2001.
70. U.S. Pat. No. 6,007,991, issued Dec. 28, 1999.
71. U.S. Pat. No. 6,506,559, issued Jan. 14, 2003.

What is claimed is:

1. A method for inhibiting binding between RAGE and a ligand thereof comprising contacting the RAGE with an agent comprising soluble RAGE G82S or a ligand-binding portion of soluble RAGE G82S.

2. The method of claim 1, wherein the agent comprises soluble RAGE G82S.

3. The method of claim 1, wherein the agent comprises a ligand-binding portion of soluble RAGE G82S.

4. A method for inhibiting binding between RAGE G82S and a ligand thereof comprising contacting the RAGE G82S with an agent comprising soluble RAGE G82S or a ligand-binding portion of soluble RAGE G82S.

5. The method of claim 4, wherein the agent comprises soluble RAGE G82S.

6. The method of claim 4, wherein the agent comprises a ligand-binding portion of soluble RAGE G82S.

7. A method for treating an inflammatory disorder in a subject comprising administering to the subject a therapeutically effective amount of an agent comprising soluble RAGE G82S or a ligand-binding portion of soluble RAGE G82S that inhibits binding between RAGE G82S and a ligand thereof.

8. The method of claim 7, wherein the inflammatory disorder is rheumatoid arthritis.

9. The method of claim 7, wherein the subject is a human.

10. The method of claim 7, wherein the agent comprises soluble RAGE G82S.

11. The method of claim 7, wherein the agent comprises a ligand-binding portion of soluble RAGE G82S.

12. A method for inhibiting the onset of an inflammatory disorder in a subject comprising administering to the subject a prophylactically effective amount of an agent comprising soluble RAGE G82S or a ligand-binding portion of soluble RAGE G82S that inhibits binding between RAGE G82S and a ligand thereof.

13. The method of claim 12, wherein the subject is a human.

14. The method of claim 12, wherein the agent comprises soluble RAGE G82S.

15. The method of claim 12, wherein the agent comprises a ligand-binding portion of soluble RAGE G82S.

* * * * *